(12) United States Patent
Mordaunt

(10) Patent No.: US 10,561,531 B2
(45) Date of Patent: *Feb. 18, 2020

(54) LASER ASSISTED CATARACT SURGERY

(71) Applicant: EXCEL-LENS, INC., Los Gatos, CA (US)

(72) Inventor: David H. Mordaunt, Los Gatos, CA (US)

(73) Assignee: EXCEL-LENS, INC., Los Gatos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/272,089

(22) Filed: Sep. 21, 2016

(65) Prior Publication Data

US 2017/0007453 A1    Jan. 12, 2017

Related U.S. Application Data

(63) Continuation of application No. 15/238,613, filed on Aug. 16, 2016, now Pat. No. 10,327,951, which is a
(Continued)

(51) Int. Cl.
*A61F 9/008*   (2006.01)
*A61B 3/00*    (2006.01)
*A61B 3/117*   (2006.01)

(52) U.S. Cl.
CPC ........ *A61F 9/00814* (2013.01); *A61B 3/0091* (2013.01); *A61B 3/1173* (2013.01);
(Continued)

(58) Field of Classification Search
CPC ...... A61F 9/008–009; A61F 2009/0087; A61F 2009/00889; A61F 2009/00897
(Continued)

(56) References Cited

U.S. PATENT DOCUMENTS 3,971,382 A   7/1976   Krasnov
3,982,541 A   9/1976   L'Esperance, Jr.
(Continued)

FOREIGN PATENT DOCUMENTS

EP    1759672 A1    3/2007
WO    1999058160 A1   11/1999
(Continued)

OTHER PUBLICATIONS

Nor, "Pachometric Study on the Influence of Corneal Endothelial Vital Staining Corneal Thickness after Cataract Extraction Studies by Vital Staining with Trypan Blue", ACTA Opthalmologica, vol. 51, 1973, pp. 679-686.
(Continued)

*Primary Examiner* — Nathan J Jenness
(74) *Attorney, Agent, or Firm* — Innovation Counsel LLP

(57) ABSTRACT

Laser assisted cataract surgery methods and devices utilize one or more treatment laser beams to create a shaped opening in the anterior lens capsule of the eye when performing a capsulorrhexis procedure. A light absorbing agent may be applied to the anterior lens capsule to facilitate laser thermal separation of tissue along a treatment beam path on the lens capsule. Relative or absolute reflectance from the eye, and optionally from a surgical contact lens, may be measured to confirm and optionally quantify the presence of the light absorbing agent, before the treatment beam is applied. Such measurements may be used to determine that sufficient light absorbing agent is present in the lens capsule so that transmission of the treatment beam through the capsule will be below a predetermined threshold deemed safe for the retina and other interior portions of the eye, and may also be used to determine that sufficient light absorbing agent is present to result in complete laser thermal separation of the anterior capsule along the treatment beam path.
(Continued)

Visualization patterns produced with one or more target laser beams may be projected onto the lens capsule tissue to aid in the capsulorrhexis procedure. In addition or alternatively, virtual visualization patterns may presented on a display integrated with a laser assisted cataract surgery device to aid in the procedure. The visual axis of the eye may be determined, during surgery for example, with a laser beam on which the patient is fixated. The orientation of a toric IOL may be assessed during or after placement by observing the reflection from the back of the eye of a laser beam on which the patient is fixated. The devices disclosed herein may be attached to or integrated with microscopes.

10 Claims, 28 Drawing Sheets

Related U.S. Application Data continuation of application No. PCT/US2015/018158, filed on Feb. 27, 2015, which is a continuation-in-part of application No. 14/193,592, filed on Feb. 28, 2014, now Pat. No. 10,206,817, and a continuation-in-part of application No. 14/193,630, filed on Feb. 28, 2014, now Pat. No. 9,820,886, and a continuation-in-part of application No. 14/193,671, filed on Feb. 28, 2014, now Pat. No. 10,231,872, and a continuation-in-part of application No. 14/193,716, filed on Feb. 28, 2014, now abandoned.

(60) Provisional application No. 62/047,373, filed on Sep. 8, 2014, provisional application No. 61/975,506, filed on Apr. 4, 2014.

(52) U.S. Cl.
CPC ........ *A61F 9/0084* (2013.01); *A61F 9/00802* (2013.01); *A61F 9/00812* (2013.01); *A61F 9/00821* (2013.01); *A61F 2009/0087* (2013.01); *A61F 2009/00857* (2013.01); *A61F 2009/00887* (2013.01); *A61F 2009/00889* (2013.01); *A61F 2009/00897* (2013.01)

(58) Field of Classification Search
USPC ........................................................ 606/4–6
See application file for complete search history.

(56) References Cited

U.S. PATENT DOCUMENTS

| | | |
|---|---|---|
| 4,367,744 A | 1/1983 | Sole |
| 4,481,948 A | 11/1984 | Sole |
| 4,538,608 A | 9/1985 | L'Esperance, Jr. |
| 4,907,586 A | 3/1990 | Bille et al. |
| 4,989,968 A * | 2/1991 | Freedman ............... A61B 3/14 351/206 |
| 5,261,923 A | 11/1993 | Soares |
| 5,283,598 A | 2/1994 | McMillan et al. |
| 5,296,787 A | 3/1994 | Albrecht et al. |
| 5,346,491 A | 9/1994 | Oertli |
| 5,350,374 A | 9/1994 | Smith |
| 5,437,658 A | 8/1995 | Muller et al. |
| 5,507,740 A | 4/1996 | O'Donnell, Jr. |
| 5,520,679 A | 5/1996 | Lin |
| 5,569,280 A | 10/1996 | Kamerling |
| 5,620,435 A | 4/1997 | Belkin et al. |
| 5,722,970 A | 3/1998 | Colvard et al. |
| 5,798,349 A | 8/1998 | Levy et al. |
| 5,860,994 A | 1/1999 | Yaacobi |
| 5,873,883 A | 2/1999 | Cozean, Jr. et al. |
| 5,947,955 A * | 9/1999 | Kadambi ............... A61F 9/008 351/205 |
| 5,958,266 A | 9/1999 | Fugo et al. |
| 5,984,916 A | 11/1999 | Lai |
| 6,010,497 A | 1/2000 | Tang et al. |
| 6,033,396 A | 3/2000 | Huang et al. |
| 6,063,073 A | 5/2000 | Peyman |
| 6,159,205 A | 12/2000 | Herekar et al. |
| 6,165,190 A | 12/2000 | Nguyen |
| 6,171,336 B1 | 1/2001 | Sawusch |
| 6,210,401 B1 | 4/2001 | Lai |
| 6,217,570 B1 * | 4/2001 | Nevyas ................. A61F 9/008 128/898 |
| 6,280,470 B1 | 8/2001 | Peyman |
| 6,325,792 B1 | 12/2001 | Swinger et al. |
| RE37,504 E | 1/2002 | Lin |
| 6,351,663 B1 | 2/2002 | Flower et al. |
| 6,367,480 B1 | 4/2002 | Coroneo |
| 6,375,449 B1 | 4/2002 | Coroneo |
| 6,520,955 B2 | 2/2003 | Reynard |
| 6,533,769 B2 | 3/2003 | Holmen |
| 6,575,962 B2 | 6/2003 | Hohla |
| 6,607,527 B1 | 8/2003 | Ruiz et al. |
| 6,673,067 B1 | 1/2004 | Peyman |
| 6,720,314 B1 | 4/2004 | Melles |
| 6,741,691 B1 | 5/2004 | Ritter et al. |
| 7,014,991 B2 | 3/2006 | Buono |
| 7,691,099 B2 | 4/2010 | Berry |
| 8,408,182 B2 | 4/2013 | Mordaunt |
| 8,562,596 B2 | 10/2013 | Mordaunt |
| 2003/0213780 A1 | 11/2003 | Fugo et al. |
| 2004/0073200 A1 | 4/2004 | Caudle |
| 2004/0111083 A1 | 6/2004 | Gross et al. |
| 2004/0206364 A1 | 10/2004 | Flower |
| 2005/0173383 A1 | 8/2005 | Coccio et al. |
| 2005/0284774 A1 | 12/2005 | Mordaunt |
| 2005/0288745 A1 | 12/2005 | Andersen et al. |
| 2006/0111697 A1 | 5/2006 | Brinkmann et al. |
| 2006/0195074 A1 | 8/2006 | Bartoli |
| 2006/0195076 A1 | 8/2006 | Blumenkranz et al. |
| 2007/0043339 A1 | 2/2007 | Horvath |
| 2007/0055156 A1 | 3/2007 | Desilets et al. |
| 2007/0091265 A1 * | 4/2007 | Kardon ................ A61B 3/0058 351/206 |
| 2007/0093868 A1 | 4/2007 | Fugo |
| 2007/0121069 A1 | 5/2007 | Andersen et al. |
| 2007/0126985 A1 | 6/2007 | Wiltberger et al. |
| 2007/0129709 A1 | 6/2007 | Andersen et al. |
| 2007/0129775 A1 | 6/2007 | Mordaunt et al. |
| 2007/0147730 A1 | 6/2007 | Wiltberger et al. |
| 2007/0189664 A1 | 8/2007 | Andersen et al. |
| 2007/0230520 A1 | 10/2007 | Mordaunt et al. |
| 2007/0265602 A1 | 11/2007 | Mordaunt et al. |
| 2008/0015553 A1 | 1/2008 | Zacharias |
| 2008/0228177 A1 | 9/2008 | Moritz |
| 2008/0249514 A1 * | 10/2008 | Hohla .................... A61F 9/007 606/5 |
| 2008/0281303 A1 | 11/2008 | Culbertson et al. |
| 2008/0284979 A1 | 11/2008 | Yee et al. |
| 2009/0069794 A1 * | 3/2009 | Kurtz ................. A61F 9/00825 606/4 |
| 2009/0088734 A1 | 4/2009 | Mordaunt |
| 2009/0137993 A1 | 5/2009 | Kurtz |
| 2010/0215066 A1 | 8/2010 | Mordaunt et al. |
| 2011/0056276 A1 | 3/2011 | Scott et al. |
| 2011/0172649 A1 | 7/2011 | Schuele et al. |
| 2011/0178511 A1 | 7/2011 | Blumenkranz et al. |
| 2011/0178512 A1 | 7/2011 | Blumenkranz et al. |
| 2011/0245817 A1 | 10/2011 | Yokosuka |
| 2012/0029489 A1 | 2/2012 | Mordaunt et al. |
| 2012/0242957 A1 | 9/2012 | Mordaunt |
| 2012/0245571 A1 | 9/2012 | Mordaunt et al. |
| 2012/0259320 A1 | 10/2012 | Loesel et al. |
| 2012/0316545 A1 | 12/2012 | Blumenkranz et al. |
| 2013/0023864 A1 | 1/2013 | Blumenkranz et al. |
| 2013/0072915 A1 | 3/2013 | Grant et al. |
| 2013/0100409 A1 | 4/2013 | Grant et al. |
| 2013/0103010 A1 | 4/2013 | Grant et al. |
| 2013/0103011 A1 | 4/2013 | Grant et al. |
| 2013/0103012 A1 | 4/2013 | Grant et al. |
| 2013/0103015 A1 | 4/2013 | Grant et al. |

(56) References Cited

U.S. PATENT DOCUMENTS

| | | |
|---|---|---|
| 2013/0197634 A1 | 8/2013 | Palanker et al. |
| 2013/0231645 A1 | 9/2013 | Mordaunt |
| 2013/0289543 A1 | 10/2013 | Mordaunt |
| 2013/0294668 A1 | 11/2013 | Mordaunt et al. |
| 2013/0345683 A1 | 12/2013 | Mordaunt et al. |
| 2014/0046310 A1 | 2/2014 | Mordaunt |
| 2014/0128686 A1 | 5/2014 | Klaffenbach et al. |
| 2014/0135749 A1 | 5/2014 | Goh et al. |
| 2014/0135751 A1 | 5/2014 | Hohla et al. |
| 2014/0228826 A1 | 8/2014 | Blumenkranz et al. |
| 2014/0228827 A1 | 8/2014 | Blumenkranz et al. |
| 2014/0257257 A1 | 9/2014 | Grant et al. |
| 2014/0316386 A1 | 10/2014 | Blumenkranz et al. |
| 2014/0347632 A1 | 11/2014 | Mordaunt |
| 2015/0009576 A1 | 1/2015 | Mordaunt et al. |
| 2015/0038951 A1 | 2/2015 | Blumenkranz et al. |
| 2015/0038952 A1 | 2/2015 | Blumenkranz et al. |
| 2015/0100049 A1 | 4/2015 | Mordaunt et al. |
| 2015/0141968 A1 | 5/2015 | Blumenkranz et al. |
| 2015/0157507 A1 | 6/2015 | Mordaunt et al. |

FOREIGN PATENT DOCUMENTS

| | | |
|---|---|---|
| WO | 2001003620 A1 | 1/2001 |
| WO | 2014039093 A1 | 3/2014 |

OTHER PUBLICATIONS

Haritoglou et al., "An Evaluation of Novel Vital Dyes for Intraocular Surgery", Investigative Ophthalmology & Visual Science, Sep. 2005, vol. 46, No. 9, pp. 3315-3322.

PCT International Search Report and Written Opinion of the ISA, PCT/US2015/018158, dated Jul. 13, 2015, 14 pages.

Fritz, Wolfram L., M.D., "Fluorescein blue, light-assisted capsulorhexis for mature or hypermature cataract", J Cataract Refract Surg—vol. 24, Jan. 1998, pp. 19-20.

Gimbel, Howard V., M.D., et al., "Development, advantages, and methods of the continuous circular capsulorhexis technique", J Cataract Refract Surg—vol. 16, Jan. 1990, pp. 31-37.

Hoffer, Kenneth J., J.D., et al., "Intracameral Subcapsular Fluorescein Staining for Improved Visualization During Capsulorhexis in Mature Cataracts", J Cataract Refract Surg—vol. 19, Jul. 1993, 1 page.

Horiguchi et al., "Staining of the Lens Capsule for Circular Continuous Capsulorrhexis in Eyes with White Cataract", Arch Ophthalmol, vol. 116, Apr. 1998, http://archopht.jamanetwork.com, Jan. 24, 2015, pp. 535-537.

Burk, Scott E., M.D., et al., "Indocyanine Green-assisted Peeling of the Retinal Internal Limiting Membrane", Association of University Professors of Ophthalmology, 2000, the American Academy of Ophthalmology, pp. 2010-2014.

Norn, "Per Operative Trypan Blue Vital Staining of Corean Endothelium Eight Years' Follow Up", ACTA Opthalmologica, vol. 58, 1980, pp. 550-555.

Norn, "Pachometric Study on the Influence of Corneal Endothelial Vital Staining Corneal Thickness after Cataract Extraction Studies by Vital Staining with Trypan Blue", Acta Opthalmologica, vol. 51, 1973, pp. 679-686.

Solomon, Kerry D., M.D., et al., "Protective Effect of the Anterior Lens Capsule during Extracapsular Cataract Extraction," Department of Ophthalmology, Medical University of South Carolina, Charleston, Aug. 1, 1988, pp. 591-597.

Melles, Gerrit, R.J., M.D., et al., "Trypan blue capsule staining to visualize the capsulorhexis in cataract surgery", J Cataract Refract Surg—vol. 25, Jul. 1999, pp. 7-9.

Chang, David F., M.D., "Trypan Blue Versus Indocyanine Green", Cataract & Refractive Surgery Today, Mar. 2005, 4 pages.

Bernstein (http://www.bernstein.eu/fileadmin/downloads/pdf/en/schaltertechnik!GP-Fussschalter_GB.pdf) accessed on Nov. 6, 2015 and backdated to Jan. 3, 2014 using https://web.archive.org/web/*/http://www.bernstein.eu/fileadmin/downloads/pdf/en/schaltertechnik!GP-Fussschalter_GB.pdf.

Kochubey et al., "Spectral Characteristics of Indocyanine Green upon Its Interaction with Biological Tissues", Optics and Spectroscopy, vol. 99, No. 4, 2005, pp. 560-566.

Graham, et al. "Experimental and theoretical study of the spectral behavior of Trypan Blue in various solvents", Journal of Molecular Structure 1040 (2013) 1-8.

Search Report corresponding the CN Application No. 201580016670.5, dated May 2, 2018, 2 pages.

\* cited by examiner

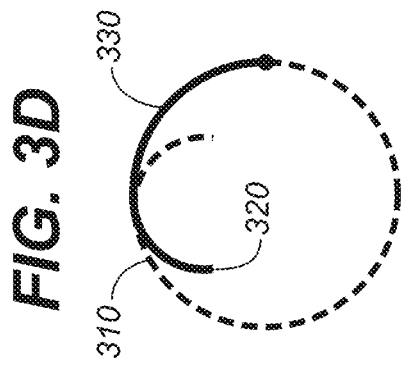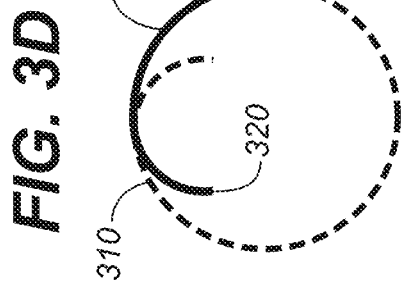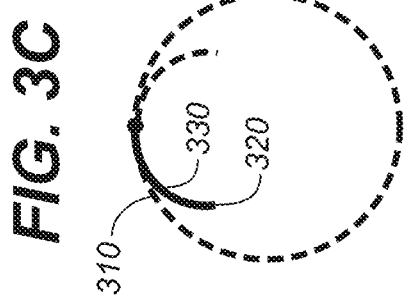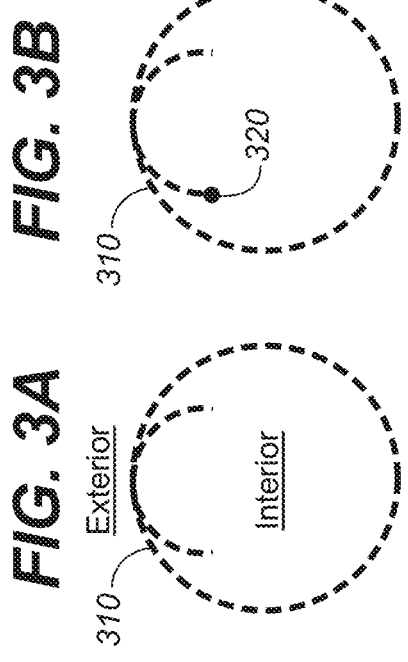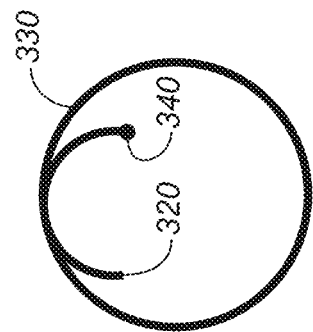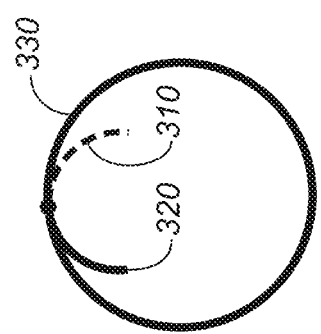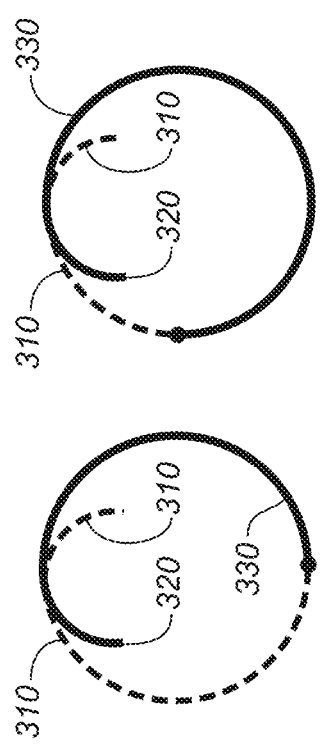

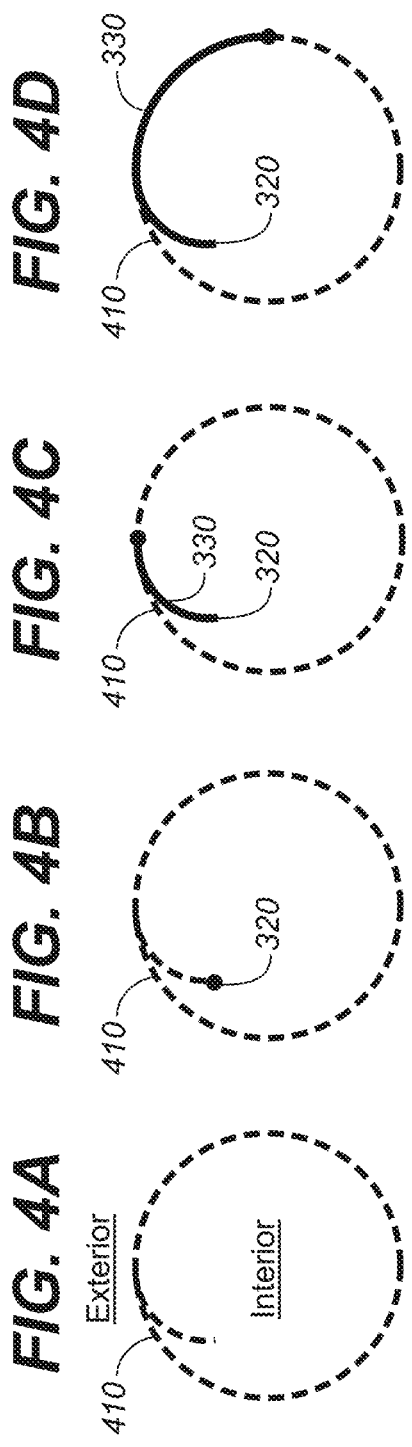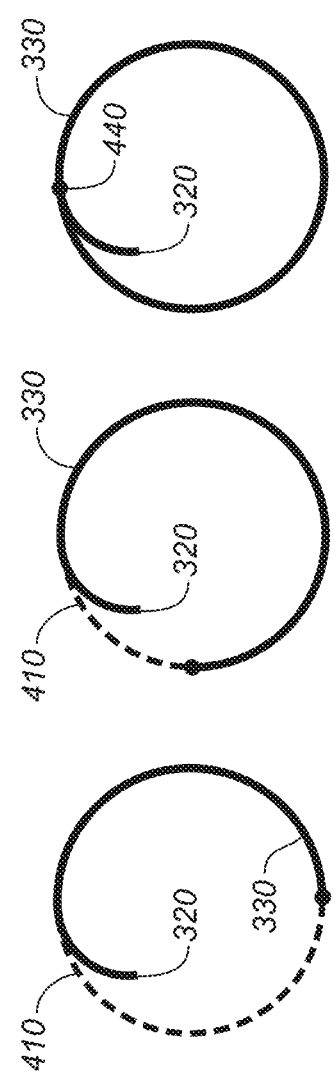

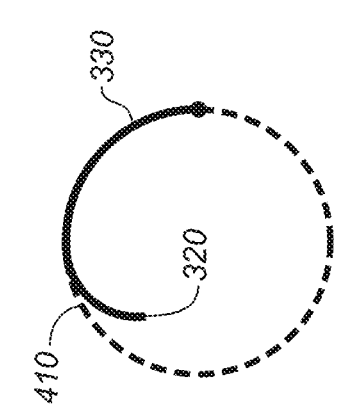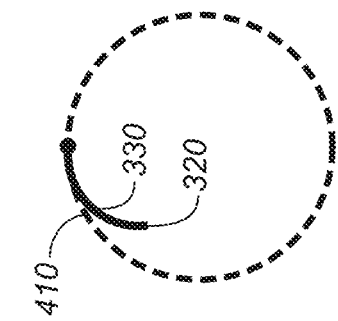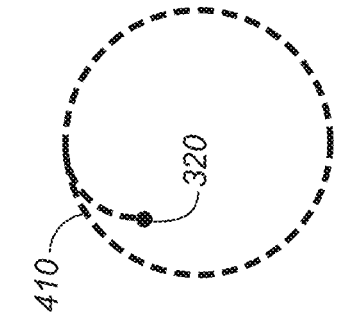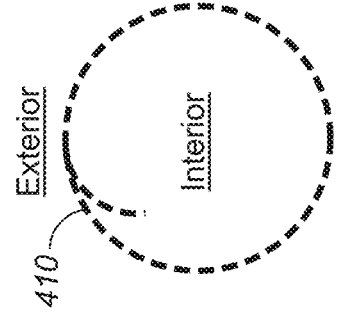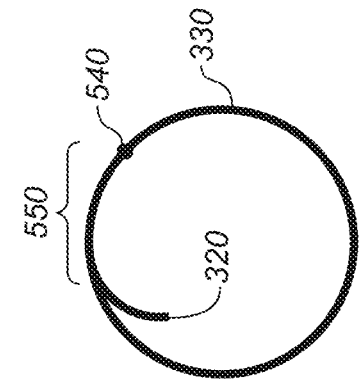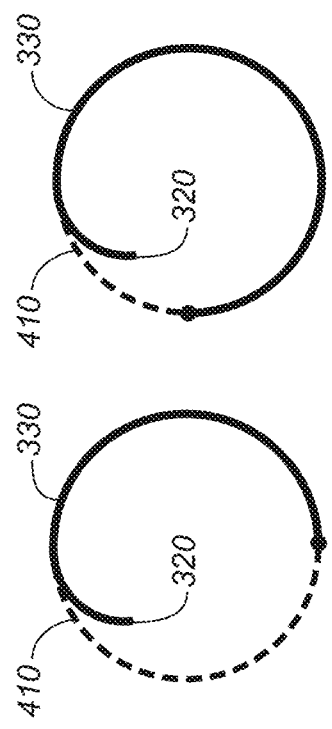

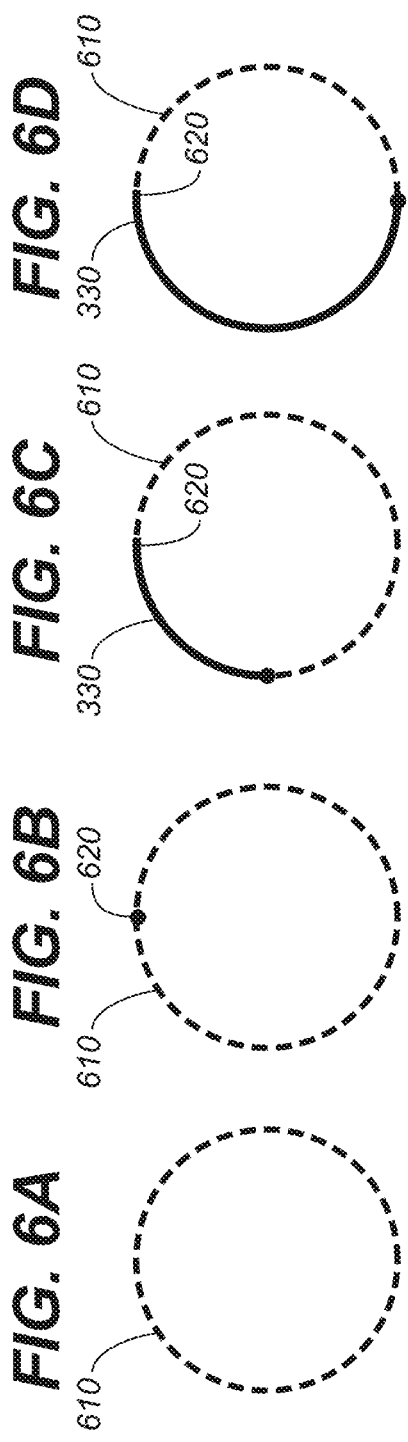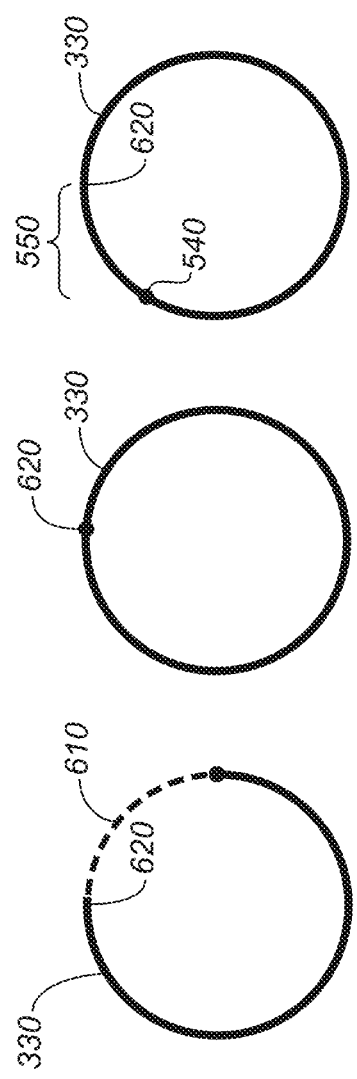

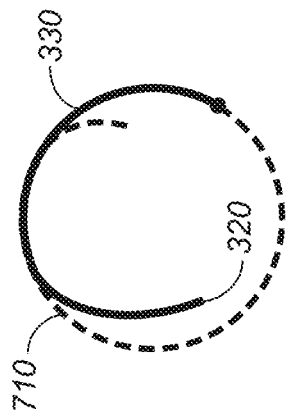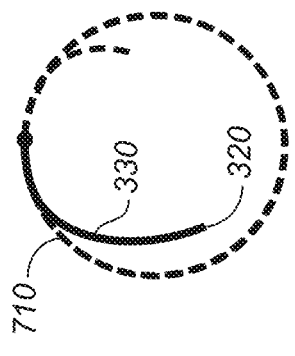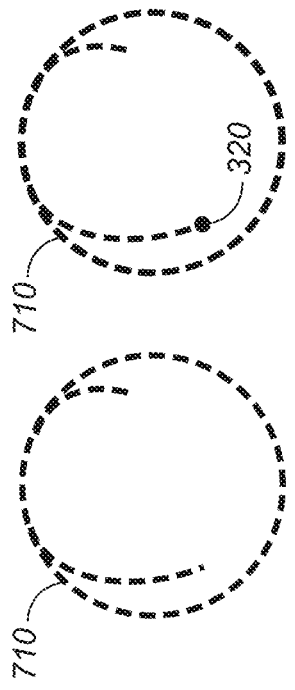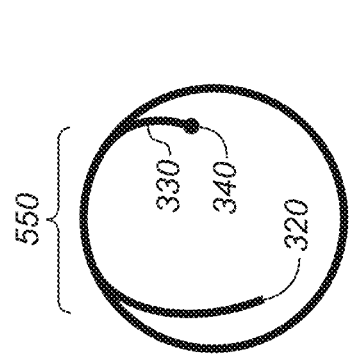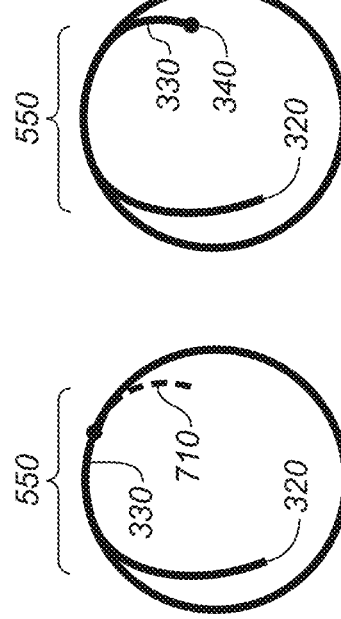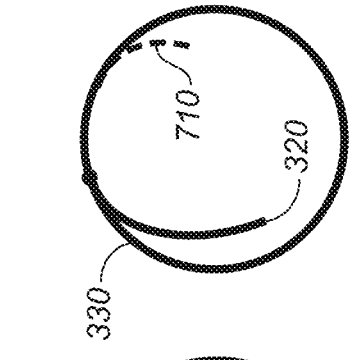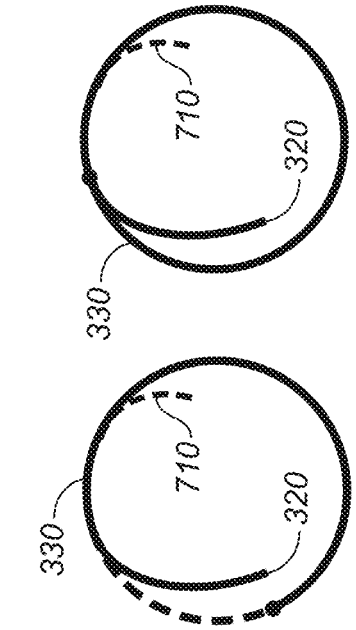

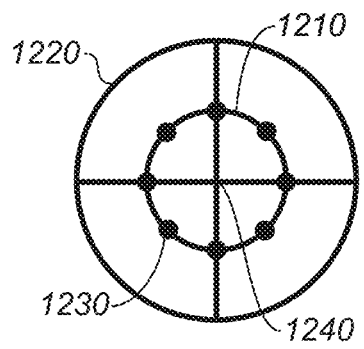 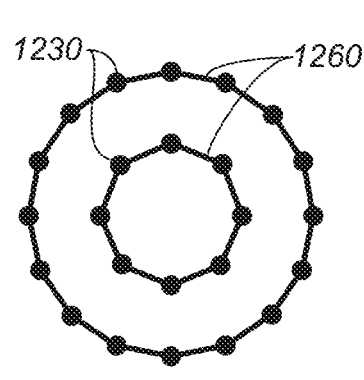 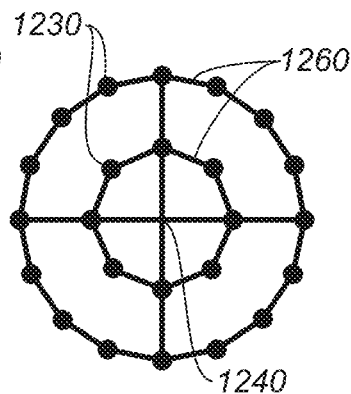
FIG. 12A     FIG. 12B     FIG. 12C
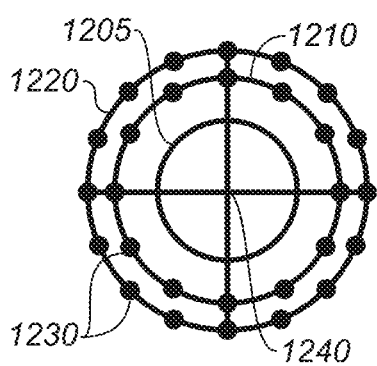 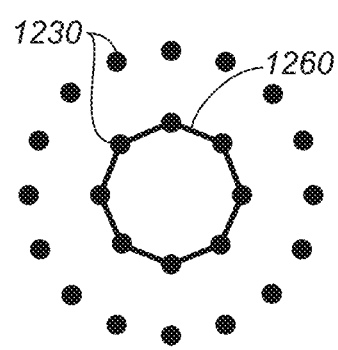 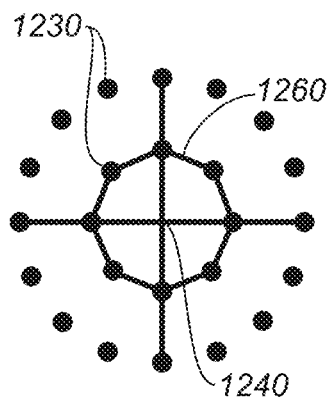
FIG. 12D     FIG. 12E     FIG. 12F

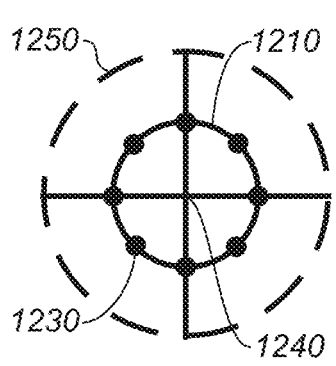
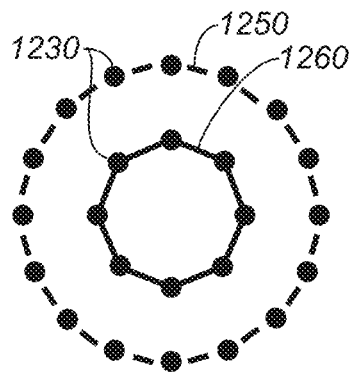
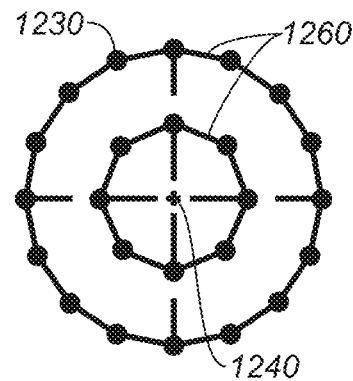
FIG. 12G    FIG. 12H    FIG. 12I
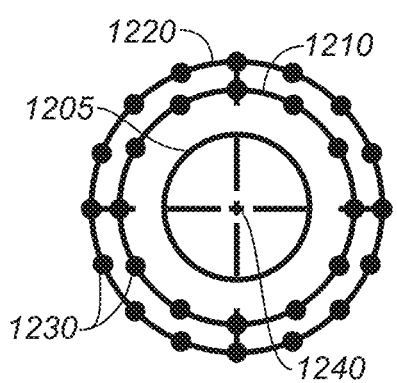
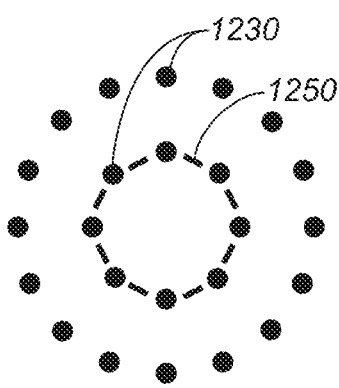
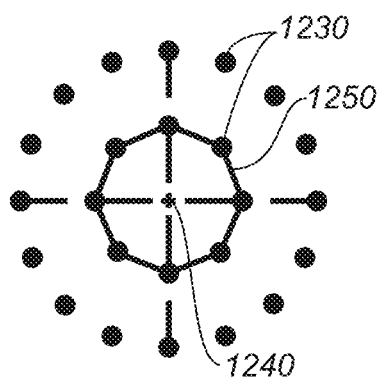
FIG. 12J    FIG. 12K    FIG. 12L

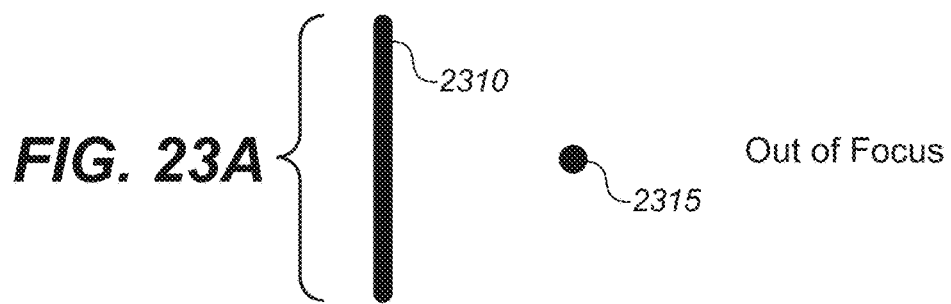
FIG. 23A — Out of Focus
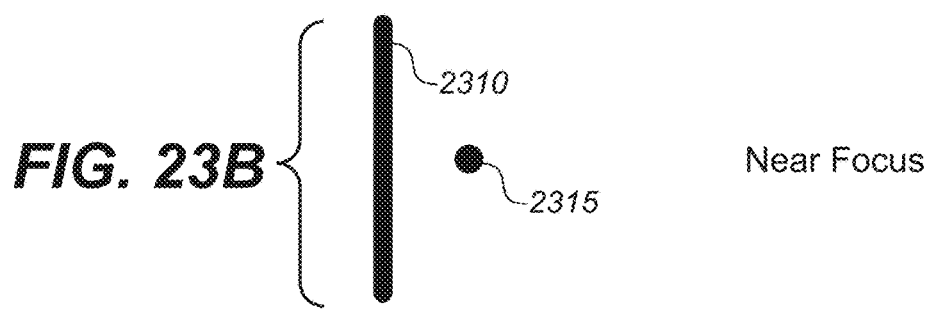
FIG. 23B — Near Focus
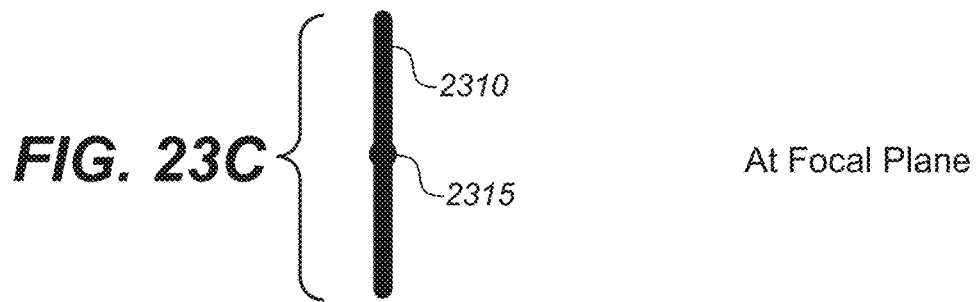
FIG. 23C — At Focal Plane
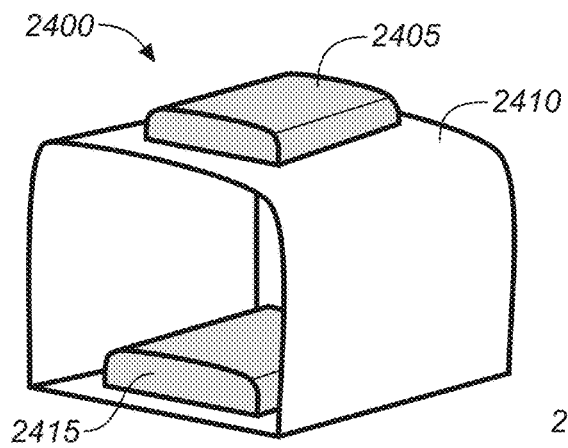
FIG. 24A
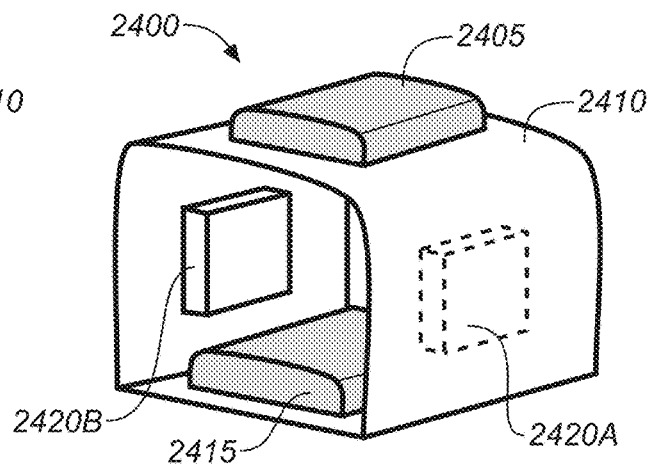
FIG. 24B

LASER ASSISTED CATARACT SURGERY

CROSS REFERENCE TO RELATED APPLICATIONS

This patent application is a Continuation of U.S. patent application Ser. No. 15/238,613 titled Laser Assisted Cataract Surgery" and filed Aug. 16, 2016, which is a Continuation of International Patent Application No. PCT/US2015/018158 titled "Laser Assisted Cataract Surgery" and filed Feb. 27, 2015. International Patent Application No. PCT/US2015/018158 claims benefit of priority from U.S. patent application Ser. No. 14/193,592 titled "Laser Assisted Cataract Surgery" filed Feb. 28, 2014, U.S. patent application Ser. No. 14/193,630 titled "Laser Assisted Cataract Surgery" filed Feb. 28, 2014, U.S. patent application Ser. No. 14/193,671 titled "Laser Assisted Cataract Surgery" filed Feb. 28, 2014, U.S. patent application Ser. No. 14/193,716 titled "Laser Assisted Cataract Surgery" filed Feb. 28, 2014, U.S. Provisional Patent Application No. 61/975,506 titled "Laser Assisted Cataract Surgery" filed Apr. 4, 2014, and U.S. Provisional Patent Application No. 62/047,373 titled "Laser Assisted Cataract" and filed Sep. 8, 2014. Each of the patent applications listed above is incorporated herein by reference in its entirety.

FIELD OF THE INVENTION

The invention relates generally to laser assisted ophthalmic surgery, and more particularly to methods and devices using one or more lasers in performing a capsulorrhexis.

BACKGROUND

Cataracts are a common cause of poor vision and are the leading cause of blindness. There are at least 100 M eyes with cataracts causing visual acuity of less than 6/60 in meters (or 20/200 in feet). Cataract extraction is the most commonly performed surgical procedure in the world with estimates of over 22 million cases worldwide and over 3 million cases being performed annually in North America. Generally, there are two types of cataract surgery: small incision cataract surgery with phacoemulsification, and extra-capsular cataract extraction.

In small incision cataract surgery with phacoemulsification, the more common approach, about a 2 millimeter (mm) incision is made in the cornea and the opacified natural lens is removed with irrigation, aspiration, and phacoemulsification while leaving the elastic lens capsule intact to allow implantation and retention of an intraocular lens (IOL). Currently, extra-capsular cataract extraction surgery is a more invasive procedure and is performed in the developing countries where there are fewer resources. In this procedure a large incision of 6 mm or more is made in the sclera, and the complete opacified natural lens is removed.

One of the more critical components of both of these surgical procedures is the capsulorrhexis (which is also referred to as the capsulotomy), which is the incision in the lens capsule made to permit removal of the lens nucleus and cortex. The lens capsule is a transparent, homogeneous basement membrane that comprises collagen. It has elastic properties without being composed of elastic fibers. The capsule has a smooth surface contour except at its equator where zonules attach.

Typically the capsulorrhexis creates a symmetric circular incision, centered about the visual axis and sized appropriately for the IOL and the patient's condition. The mechanical integrity around the newly formed incision edge needs to be sufficient to withstand the forces experienced during cataract extraction and IOL implantation. Postoperatively, the newly formed capsule rim hardens and the opening contracts, providing further strength and structural support for the IOL to prevent dislocation and misalignment.

The current standard of care for capsulorrhexis is Continuous Curvilinear Capsulorrhexis (CCC). The concept of CCC is to provide a smooth continuous circular opening through the anterior lens capsule for phacoemulsification and insertion of the intraocular lens, minimizing the risk of complications including errant tears and extensions. Currently, the capsulorrhexis is performed manually utilizing forceps or a needle. This technique depends on applying a shear force and minimizing in-plane stretching forces to manually tear the incision. One complication that may develop when performing a capsulorrhexis in this manner is an errant tear. Errant tears are radial rips and extensions of the capsulorrhexis towards the capsule equator. If an errant tear encounters a zonular attachment the tear may be directed out to the capsular fornix and possibly through to the posterior of the capsule. Posterior capsule tears facilitate the nucleus being "dropped" into the posterior chamber, resulting in further complications.

Further problems that may develop in capsulorrhexis are related to inability of the surgeon to adequately visualize the capsule due to lack of red reflex (reddish reflection of light from the retina), to grasp it with sufficient security, or to tear a smooth symmetric circular opening of the appropriate size. Additional difficulties may relate to maintenance of the anterior chamber depth after initial opening, small size of the pupil, or the absence of a red reflex due to the lens opacity. Additional complications arise in older patients with weak zonules and very young children that have very soft and elastic capsules, which are very difficult to mechanically rupture.

Following cataract surgery there is a rapid 1-2 day response where the capsule hardens and capsule contraction starts. This contraction continues over a 4-6 week period where fibrosis of the capsulorrhexis and IOL optic interface and of the IOL haptic and capsule interfaces also occurs. Even beyond one year the capsule continues to contract to a lesser degree. Thus positioning the capsulorrhexis is a critical factor in the long-term success.

Accordingly, there is a need in the art to provide new ophthalmic methods, techniques and devices to advance the standard of care for capsulorrhexis.

SUMMARY

This specification discloses laser assisted ophthalmic surgery methods and devices.

In one aspect, a device for creating an opening in the anterior lens capsule of the eye comprises a scanning treatment laser beam having a programmed scan profile for a predetermined treatment pattern that forms a closed curve at the anterior lens capsule. The treatment laser has a wavelength selected to be strongly absorbed at the anterior lens capsule and a power selected to cause thermal denaturing of collagen in the anterior lens capsule resulting in thermal tissue separation along the closed curve without ablating anterior lens capsule tissue. The device also comprises a scanning visualization laser beam having a programmed scan profile for a predetermined visualization pattern at the anterior lens capsule and a wavelength in the visible spectrum.

The visualization pattern differs from the treatment pattern in size and geometry. At least a portion of the visualization pattern may, for example, indicate desired boundaries of the opening to be created in the anterior lens capsule and thereby facilitate aligning the treatment pattern on the anterior lens capsule. Typically, the desired boundaries of the opening differ in location from the closed curve of the treatment pattern as a result of contraction of anterior lens capsule tissue adjacent to the closed curve during and after thermal tissue separation. Alternatively, or in addition, at least a portion of the visualization pattern may correspond to one or more anatomical features of the eye, and thereby facilitate aligning the treatment pattern with respect to those anatomical features.

In another aspect, a device for creating an opening in the anterior lens capsule of the eye comprises a treatment laser beam and a two-dimensional scanner on which the treatment laser beam is incident. The scanner has a programmed scan profile for a predetermined treatment pattern in which the treatment laser beam is scanned to form a closed curve at the anterior lens capsule. The device comprises a lens positioned to focus the treatment laser beam to a waist at the anterior lens capsule, with the treatment beam expanding from its waist to be defocused on the retina of the eye. The treatment pattern passes through a treatment pattern invariant and/or a treatment pattern waist between the lens and the eye. The treatment laser beam has a wavelength selected to be strongly absorbed at the anterior lens capsule and a power selected to cause thermal denaturing of collagen in the anterior lens capsule resulting in thermal tissue separation along the closed curve of the treatment pattern without ablating anterior lens capsule tissue.

The treatment pattern may diverge in the eye and consequently be expanded in size and area on the retina compared to its size and area at the anterior lens capsule. As a result, the treatment pattern may avoid the fovea on the retina.

In another aspect, a device for creating an opening in the anterior lens capsule of the eye comprises a continuous wave scanning treatment laser beam having a programmed scan profile for a predetermined treatment pattern forming a closed curve at the anterior lens capsule in a single pass. The treatment laser has a wavelength selected to be strongly absorbed at the anterior lens capsule, and a power selected to cause thermal denaturing of collagen in the anterior lens capsule resulting in thermal tissue separation along the closed curve without ablating anterior lens capsule tissue. At the beginning of the treatment pattern the power of the treatment laser ramps up from about zero to about 90% of its full power during a period of about 5 milliseconds to about 200 milliseconds. This ramp-up may minimize the likelihood of the capsule tearing at the starting point of the treatment pattern by allowing the tissue near the starting point of the pattern to initially stretch without separating, thereby reducing the shear stress/tension at the start of the pattern, and/or by avoiding or minimizing local shock waves in the fluid adjacent to the target tissue that might otherwise be generated by the growth and collapse of one or more vapor bubbles accompanying a faster thermal turn-on.

In another aspect, a device for creating an opening in the anterior lens capsule of the eye comprises a treatment laser beam and a two-dimensional scanner on which the treatment laser beam is incident. The scanner has a programmed scan profile for a predetermined treatment pattern in which the treatment laser beam is scanned to form a closed curve at the anterior lens capsule. The device comprises a lens positioned to focus the treatment laser beam to a waist at the anterior lens capsule, with the treatment laser beam expanding from its waist to be defocused on the retina of the eye. The treatment laser beam has a wavelength selected to be strongly absorbed at the anterior lens capsule and a power selected to cause thermal denaturing of collagen in the anterior lens capsule resulting in thermal tissue separation along the closed curve of the treatment pattern without ablating anterior lens capsule tissue. The device also comprises a first visible light visualization laser beam sharing an optical path with the treatment laser beam, and a second visible light visualization laser beam intersecting the first visualization laser beam at or approximately at the waist of the treatment laser beam.

The first visualization laser beam and the second visualization laser beam may be produced, for example, from a single visible light laser beam incident on the scanner by dithering the scanner between the optical path of the first visualization laser beam and the optical path of the second visualization laser beam.

In another aspect, virtual visualization patterns may be presented on a display and overlaid with a view of the anterior lens capsule to aid in the ophthalmic surgical procedures described herein. Such virtual visualization patterns may be used instead of, or in addition to, the projected visualization patterns described herein.

In another aspect, the visual axis of the patient's eye may be determined before or during an ophthalmic surgical procedure by having the patient fixate on (look directly into) a low power laser beam. Optionally, the laser beam may blink at a frequency perceptible by the patient to facilitate fixation on the beam.

In another aspect, the orientation of a toric IOL implanted in a patient's eye may be assessed by having the patient fixate on a low power laser beam and observing a reflection of the laser beam from the back of the patient's eye through the toric IOL.

In another aspect, relative or absolute reflectance from an eye may be measured to confirm and optionally quantify the presence of a light absorbing agent in or on the anterior lens capsule. Such measurements may be used to determine that sufficient light absorbing agent is present in the lens capsule so that transmission of the treatment beam through the capsule will be below a predetermined threshold deemed safe for the retina and other interior portions of the eye. Such measurements may also be used to determine that sufficient light absorbing agent is present to result in complete laser thermal separation of the anterior capsule along the treatment beam path, when the selected/preprogrammed treatment beam parameters are applied. These determinations may utilize a correlation between transmission of the treatment beam through the capsule and reflectance from the capsule at the treatment wavelength or another wavelength. Additionally, or alternatively, the reflectance measurements and their correlation with transmission of the treatment beam through the lens capsule may be used to optimize treatment parameters such as, for example, treatment beam power, spot diameter, and scanning speed.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIGS. 3A-3H show a view from the anterior direction of a lens capsule illustrating an example "Interior-Closed-Curve-Interior" treatment pattern in which the treatment laser beam is directed along a predetermined closed curve 310.

FIGS. 4A-4G show a view from the anterior direction of a lens capsule illustrating an example "Interior-Closed-Curve" treatment pattern in which the treatment laser beam is directed along a predetermined closed curve 410.

FIGS. 5A-5H show a view from the anterior direction of a lens capsule illustrating an example "Interior-Closed-Curve-Overlap" treatment pattern in which the treatment laser beam is directed along a predetermined closed curve 410.

FIGS. 6A-6G show a view from the anterior direction of a lens capsule illustrating an example "Closed-Curve-Overlap" treatment pattern in which the treatment laser beam is directed along a predetermined closed curve 610.

FIGS. 7A-7H show a view from the anterior direction of a lens capsule illustrating an example "Interior-Closed-Curve-Overlap-Interior" treatment pattern in which the treatment laser beam is directed along a predetermined closed curve 710.

FIGS. 12A-12L show additional visualization patterns each of which may comprise a combination of closed curves, 1205, 1210, 1220, 1260, dots 1230 on the curves, and a cross-hair 1240.

FIG. 18A shows a ray trace in the absence of a surgical contact lens, and FIGS. 18B-18C show ray traces in the presence of two different surgical contact lenses.

FIGS. 23A-23C show views of two superimposed visualization patterns produced by the device of FIG. 22 as the depth alignment of the device is adjusted.

FIGS. 24A-24B show two example foot-operable controls that may be used to control the device of FIG. 22.

DETAILED DESCRIPTION

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used in this specification and the appended claims, the singular forms "a," "an," and "the" include plural referents unless the context clearly indicates otherwise.

As described in more detail below, this specification discloses ophthalmic surgery methods and devices that utilize one or more treatment laser beams to create a shaped opening in the anterior lens capsule of the eye when performing a capsulorrhexis procedure. In the procedure, a light absorbing agent may optionally be added onto or into the lens capsule tissue, and the treatment laser wavelength selected to be strongly absorbed by the light absorbing agent. Alternatively, the treatment laser wavelength may be selected to be absorbed or strongly absorbed by the tissue itself, in which case no additional light absorbing agent need be used. In either case, as used herein the phrase "strongly absorbed" is intended to mean that transmission of the treatment beam through the tissue to be treated (e.g., the anterior lens capsule) is less than about 65%, or less than about 40%, or less than about 30%, or less than about 20%, or less than about 15%, or less than about 10%. For example, in some variations the treatment beam is strongly absorbed such that transmission through the tissue to be treated is about 11%+/−3%. The treatment laser beam is directed at the lens capsule tissue along a predetermined closed curve to cause a thermal effect in the tissue resulting in separation of the tissue along the laser beam path. The predetermined closed curve may have, for example, a circular or elliptical shape. Any other suitable shape for the closed curve may also be used. Typically, the shape is selected to reduce the likelihood of tears developing during cataract surgery, on the edge of the separated edge of the tissue that is formed exterior to the closed curve. Visualization patterns produced with one or more target laser beams may be projected onto the lens capsule tissue to aid in the procedure.

Figure 1:
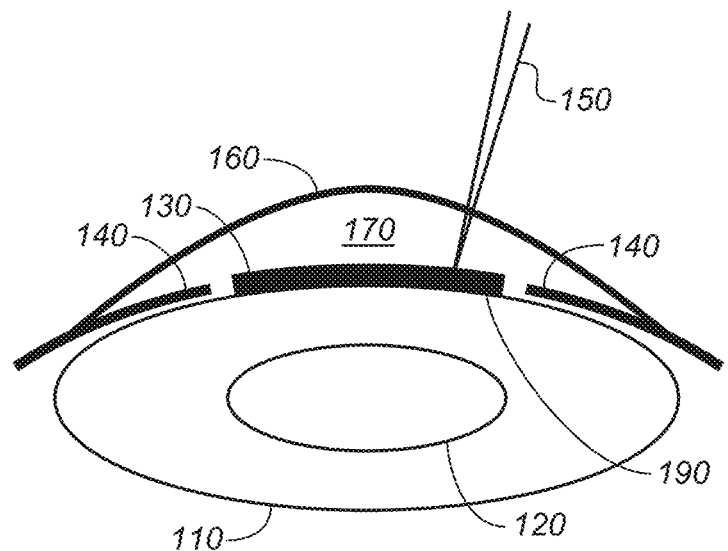
FIG. 1 shows a transverse plane view of some parts of an eye (lens capsule 110, dilated iris 140, cornea 160, anterior chamber 170, and pupil 190), the natural crystalline lens location and the intended location of an implanted intraocular lens 120, a light absorbing agent 130, and a treatment light beam 150 to be used in an example of the capsulorrhexis procedure described herein.
Figure 2:
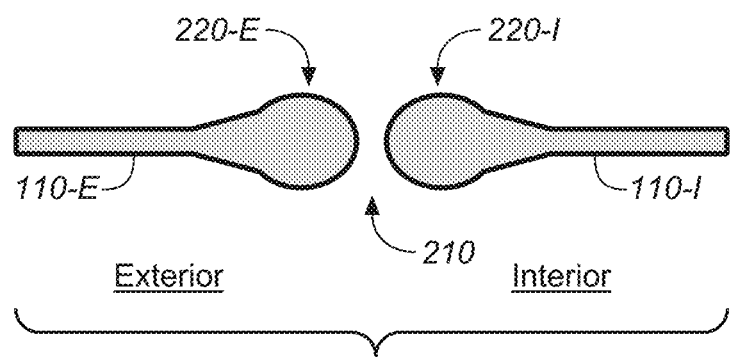
FIG. 2 shows a side view of the lens capsule 110 of FIG. 1 wherein lens capsule 110 has been separated at location 210 into two parts, e.g. an exterior part 110-E and an interior part 110-I, by a laser based method as described herein. This figure also shows the contracted and shrunken ends 220-E and 220-I bordering the separation.

General aspects of these methods and devices may be better understood with reference to FIG. 1 and FIG. 2. FIG. 1 shows, in a transverse plane view of an eye (including lens capsule 110, dilated iris 140, cornea 160, anterior chamber 170, and pupil 190), the intended location of an intraocular lens 120 to be implanted after a capsulorrhexis procedure. In the illustrated example, a light absorbing agent 130 is added into or onto a layer of the anterior lens capsule 110. This agent may be a biocompatible agent (e.g. Indocyanine green or Trypan Blue), a dye, pigment, a nanoparticle, a carbon particle, or any other suitable light absorbing agent. The light absorbing agent may be Trypan Blue, other Vital Dyes, or Indocyanine Green, for example. Subsequently, a light beam 150, e.g. a laser beam, is directed along a closed curve path on the anterior lens capsule. The directed light beam is absorbed by the light absorbing agent to deposit thermal energy in and cause a local thermal effect on the anterior lens capsule to yield a capsulorrhexis.

Referring now to FIG. 2, generally the wavelength, power, speed of light beam movement along the closed curve, and spot size on the treated tissue are selected so that the light beam can be absorbed by the light absorbing agent to deposit sufficient thermal energy adjacent to or at the anterior lens capsule to cause a mechanical separation 210 in the anterior lens capsule. The laser beam parameters are typically selected to avoid ablation of the tissue, and the mechanical separation is believed to result instead from thermal denaturing of collagen in the tissue (in which, for example, the collagen transitions from a crystalline helical structure to an amorphous structure). The denatured collagen shrinks and contracts to form thickened rims 220-E and 220-I bordering the separation forming the capsulorrhexis. Advantageously, these rims may be more elastic and resistant to tearing than the original membrane.

For clarity and convenience, various features and aspects of the inventive methods and devices are described below under separately labeled headings. This organization of the description is not meant to be limiting. Variations of the methods and devices described herein may include or employ any suitable combination of aspects or features described under the separate headings.

Treatment Beam Patterns

FIGS. 3A-3H illustrate an example "Interior-Closed-Curve-Interior" treatment pattern in which the treatment laser beam is directed along a predetermined closed curve 310. The treatment pattern starts interior to the closed curve, progresses around the closed curve, then terminates interior to the closed curve. Although illustrated as clockwise, this pattern may also be counterclockwise. Dashed line 310 of FIG. 3A represents the complete pattern. The dot 320 in FIG. 3B indicates the start point of the pattern on the interior of the closed curve, and FIGS. 3C-3H illustrate the progression of the pattern with a solid line 330 at subsequent time intervals through the delivery of the pattern. Dot 340 in FIG. 3H indicates the end point of the treatment pattern on the interior of the closed curve. Locating the start and end points of the procedure on the interior of the closed curve (in material which will be removed from the eye) helps prevent irregularities in the shape of the curve that might promote tearing of the rim of the remaining anterior lens capsule located exterior to the closed curve.

FIGS. 4A-4G illustrate an example "Interior-Closed-Curve" treatment pattern in which the treatment laser beam is directed along a predetermined closed curve 410. The treatment pattern starts interior to the closed curve, progresses around the closed curve, and then terminates on the closed curve. Although illustrated as clockwise, this pattern may also be counterclockwise. Dashed line 310 of FIG. 4A represents the complete pattern. The dot 320 in FIG. 4B indicates the start point of the pattern on the interior of the closed curve, and FIGS. 4C-4G illustrate the progression of the pattern with a solid line 330 at subsequent time intervals through the delivery of the pattern. Dot 440 in FIG. 4G indicates the end point of the treatment pattern on the closed curve.

FIGS. 5A-5H illustrate an example "Interior-Closed-Curve-Overlap" treatment pattern in which the treatment laser beam is directed along a predetermined closed curve 410. The treatment pattern starts in the interior region of the closed curve, progresses around the closed curve with a region of overlap on the closed curve, and then terminates on the closed curve. Although illustrated as clockwise, this pattern may also be counterclockwise. Dashed line 410 of FIG. 5A represents the complete pattern. The dot 320 in FIG. 5B indicates the start point of the pattern on the interior of the closed curve, and FIGS. 5C-5H illustrate the progression of the pattern with a solid line 330 at subsequent time intervals through the delivery of the pattern. Dot 540 in FIG. 5H indicates the end point of the treatment pattern on the closed curve, where the region 550 on the closed curve experiences treatment exposure of the laser near the beginning of the pattern, and again towards the later part of the pattern delivery, i.e., it is the overlap region.

FIGS. 6A-6G illustrate an example "Closed-Curve-Overlap" treatment pattern in which the treatment laser beam is directed along a predetermined closed curve 610. The treatment pattern starts on the closed curve, progresses around the closed curve with a region of overlap on the closed curve, and then terminates on the closed curve. Although illustrated as counterclockwise, this pattern may also be clockwise. Dashed line 610 of FIG. 6A represents the complete pattern. Dot 620 in FIG. 6B indicates the start point on the closed curve, and FIGS. 6C-6G illustrate the progression of the pattern with a solid line 330 at subsequent time intervals through the delivery of the pattern. Dot 540 in FIG. 6G indicates the end point of the treatment pattern on the closed curve, where the region 550 on the closed curve experiences treatment exposure of the laser near the beginning of the pattern, and again towards the later part of the pattern delivery, i.e., it is the overlap region.

FIGS. 7A-7H illustrate an example "Interior-Closed-Curve-Overlap-Interior" treatment pattern in which the treatment laser beam is directed along a predetermined closed curve 710. The treatment pattern starts interior to the closed curve, then progresses around the closed curve with a region of overlap on the closed curve, and then terminates on the interior of the closed curve. Although illustrated as clockwise, this pattern may also be counterclockwise. Dashed line 710 of FIG. 7A represents the complete pattern. Dot 320 in FIG. 7B indicates the start point on the interior of the closed curve, and FIGS. 7C-7H illustrate the progression of the pattern with a solid line 330 at subsequent time intervals through the delivery of the pattern. As shown in FIGS. 7G-7H, region 550 on the closed curve experiences treatment exposure of the laser near the beginning of the pattern, and again towards the later part of the pattern delivery, i.e., it is the overlap region. Dot 340 in FIG. 7H indicates the end point of the treatment pattern on the interior of the closed curve.

Any other suitable treatment beam patterns may also be used. One or more treatment beam pattern shapes may be preprogrammed into a laser capsulorrhexis device (described in more detail below) by the manufacturer, for example. At or prior to the time of treatment an operator may then, for example, select the size (e.g., diameter) and shape of the closed curve defining the treatment pattern, or of the desired rhexis to be produced by the closed curve of the treatment pattern.

Visualization/Target Patterns

As noted above, visualization patterns produced with one or more laser beams, which typically differ in wavelength from the treatment beam, may be projected onto the lens capsule tissue to aid in the treatment procedure. The shape and diameter of the visualization pattern may differ from that of the treatment beam pattern. Although the visualization pattern or portions of the visualization pattern may overlie the closed curve of the treatment pattern to indicate at least portions of the path to be taken by the treatment beam, this is not required. Instead, or in addition, at least part of the visualization pattern may overlie the intended location of the outer rim of the opening that will be produced by the tissue-separating treatment beam, or otherwise indicate the desired outcome of the treatment. The location of that outer rim typically differs from and is of larger diameter than the closed curve of the treatment beam pattern for two reasons: (i) the lens capsule tissue is under tension when in the eye (very much like a drum skin), so as the tissue along the closed curve is separated the exterior portion is under tension and pulled peripherally, thus enlarging the diameter; (ii) the mechanism of action for the treatment laser is to locally heat the irradiated anterior capsule on a closed curve, this heating tends to cause the collagen tissue to contract, shrink, and separate exteriorly and interiorly away from the heated closed curve. Alternatively, or in addition, at least part of the visualization pattern may correspond to one or more particular anatomical features of the eye. This may facilitate centering of the visualization pattern (and thus the treatment beam pattern) on the anatomy of the eye, or otherwise facilitate aiming the visualization and treatment beams. The visualization pattern may optionally include a cross-hair.

Figure 8:
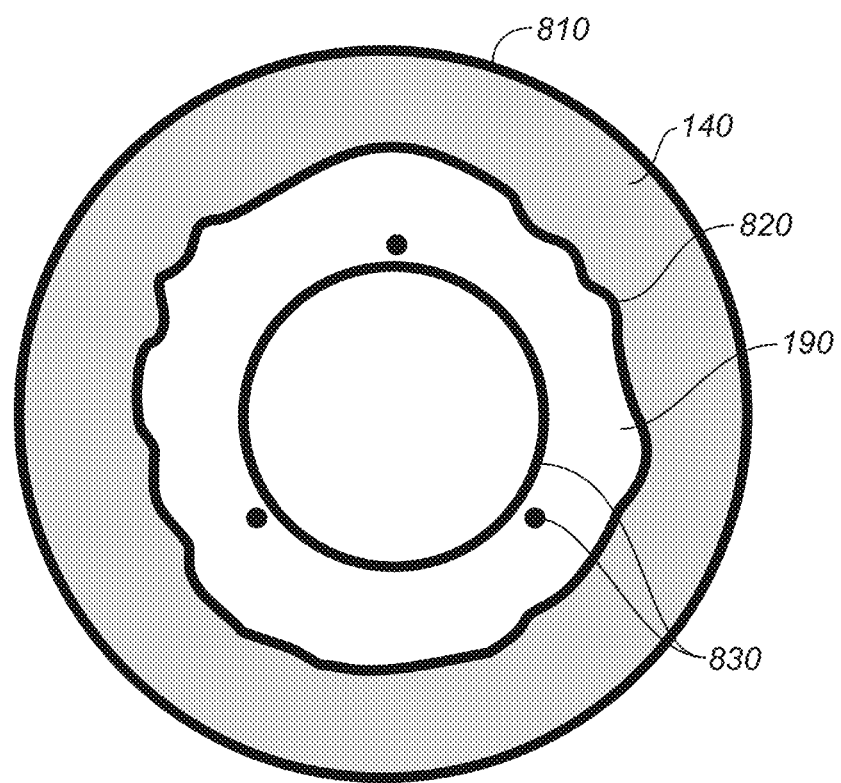
FIG. 8 shows a view of the eye with the limbus 810, iris 140, interior boundary of the iris 820, pupil 190, and a visualization pattern comprising a predetermined closed curve and at least three dots 830 that are used to assist in locating the position of the desired capsulorrhexis.

FIG. 8 illustrates an example visualization pattern 830 comprising a closed curve and at least three dots that may be used to assist in locating the desired location for a capsulorrhexis. The figure also identifies the limbus 810, iris 140, interior boundary of the iris 820, and pupil 190 of the eye to be treated.

Figure 9A:
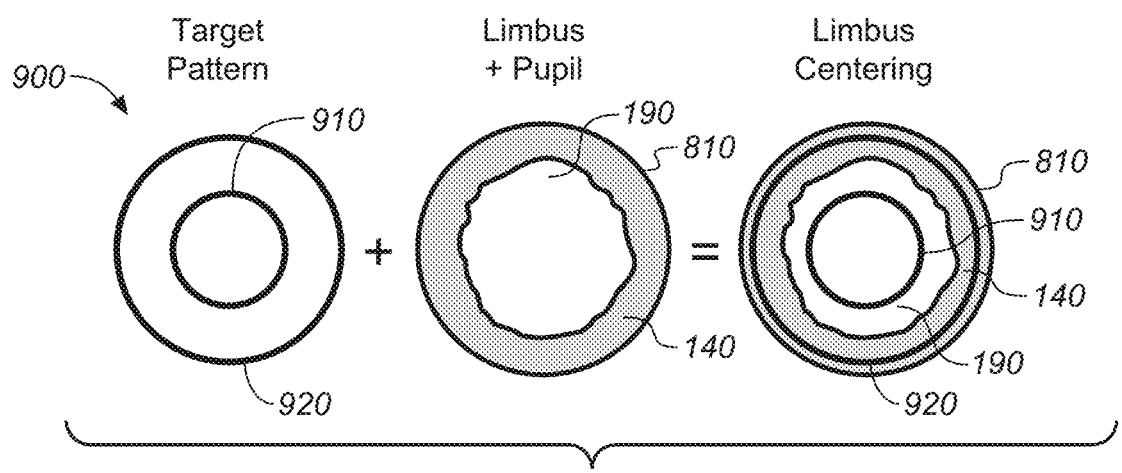
FIGS. 9A-9B show views of the eye including the limbus 810, iris 140, and pupil 190 on which are superimposed two additional example visualization patterns, each of which comprises two circles or closed curves, 910 and 920.
Figure 9B:
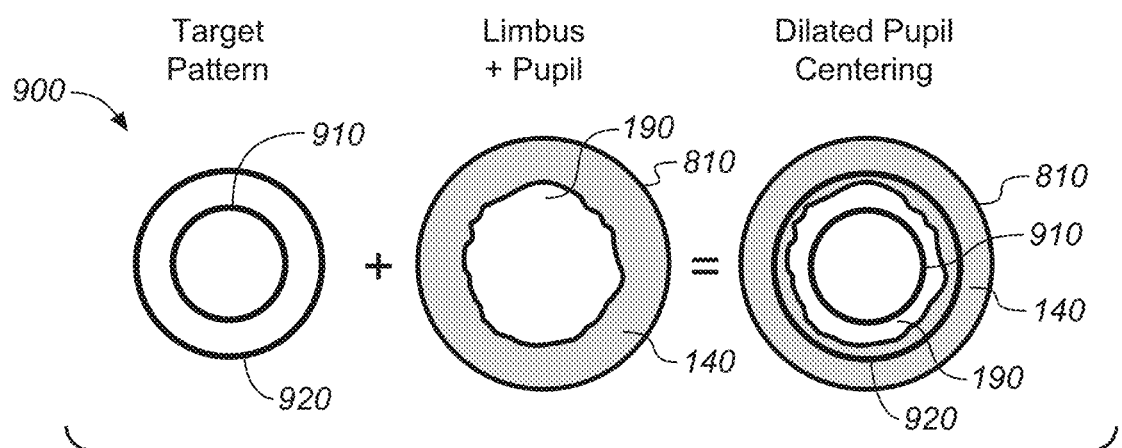

FIGS. 9A-9B each show a view of an eye including the limbus 810, iris 140, and pupil 190 onto which is projected an example visualization pattern 900 comprising two concentric circles or closed curves 910 and 920. The inner circle or closed curve 910 represents the size and location of the desired opening in the anterior capsulorrhexis. The outer circle 920, which may be sized independently of the inner circle size, may be used to center the capsulorrhexis on the limbus as illustrated in FIG. 9A. Alternatively, the outside circle may be sized to allow the centering on the interior boundary of the dilated pupil, as represented in FIG. 9B.

Figure 10A:
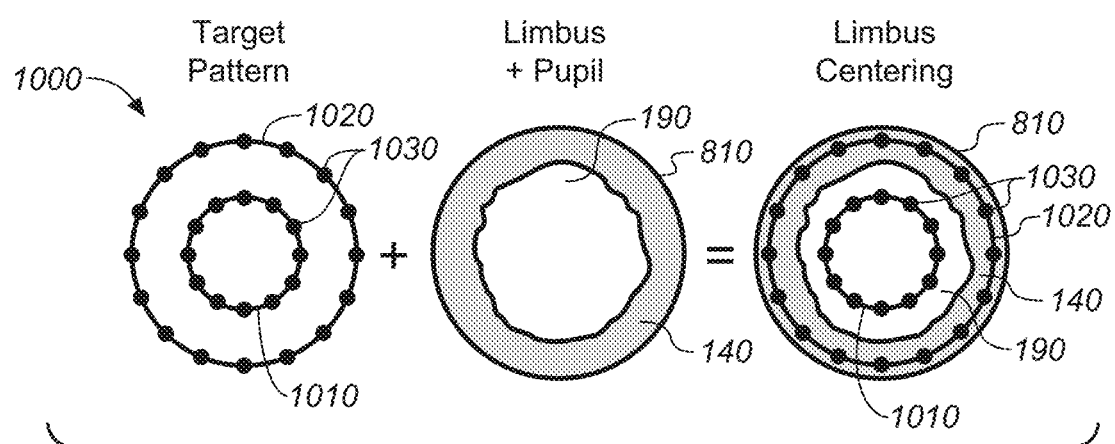
FIGS. 10A-10B show views of the eye including the limbus 810, iris 140, and pupil 190 on which are superimposed two additional example visualization patterns, each of which comprises two circles or closed curves 1010 and 1020 with dots 1030 on the curves.
Figure 10B:
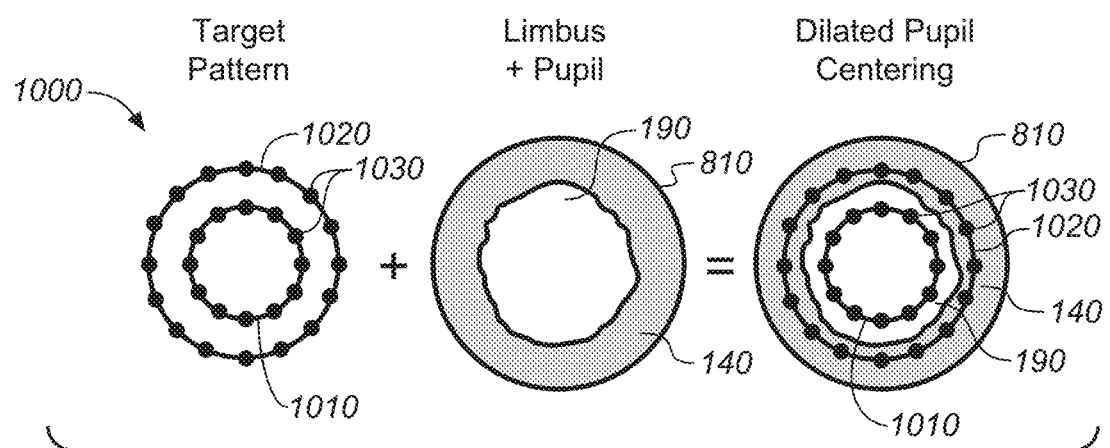

FIGS. 10A-10B each show a view of an eye including the limbus 810, iris 140, and pupil 190 onto which is projected an example visualization pattern 1000 comprising two concentric circles or closed curves 1010 and 1020 with dots 1030 on the curves. The combination of straight and/or curved lines and dots provides a pattern easily focused on the target tissue. The lines are produced by moving the visualization beam along the desired pattern. The dots are produced by dwelling the visualization beam for longer periods at the dot locations in the scan pattern. The dots may provide enhanced visualization on the target tissue because they are more intense than the lines. The inner circle or closed curve 1010 represents the size and location of the desired opening in the anterior capsulorrhexis. The outer circle 1020, which may be sized independently of the inner circle size, may be used to center the capsulorrhexis on the limbus as illustrated in FIG. 10A. Alternatively, the outside circle may be sized to facilitate centering on the interior boundary of the dilated pupil, as represented in FIG. 10B.

Figure 11A:
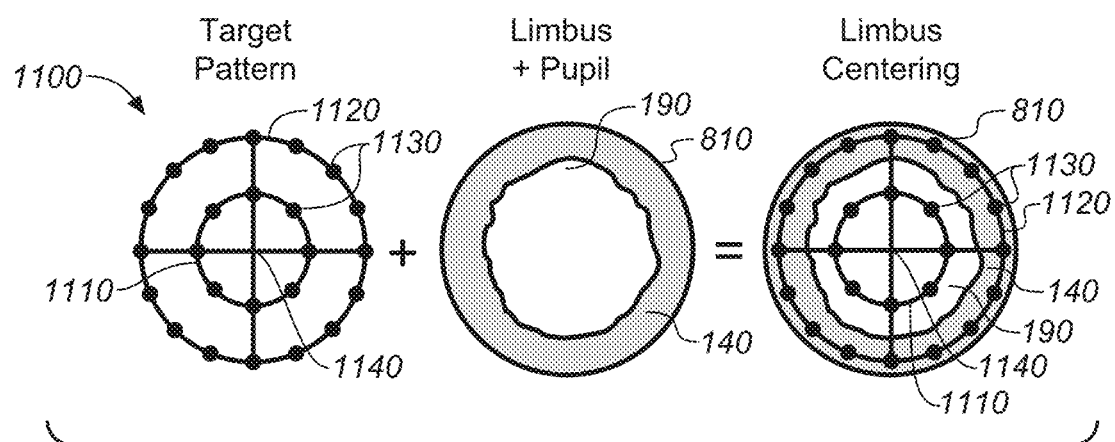
FIGS. 11A-11B show views of the eye including the limbus 810, iris 140, and pupil 190 on which are superimposed two additional example visualization patterns, each of which comprises a cross-hair and two circles or closed curves with dots on the curves.
Figure 11B:
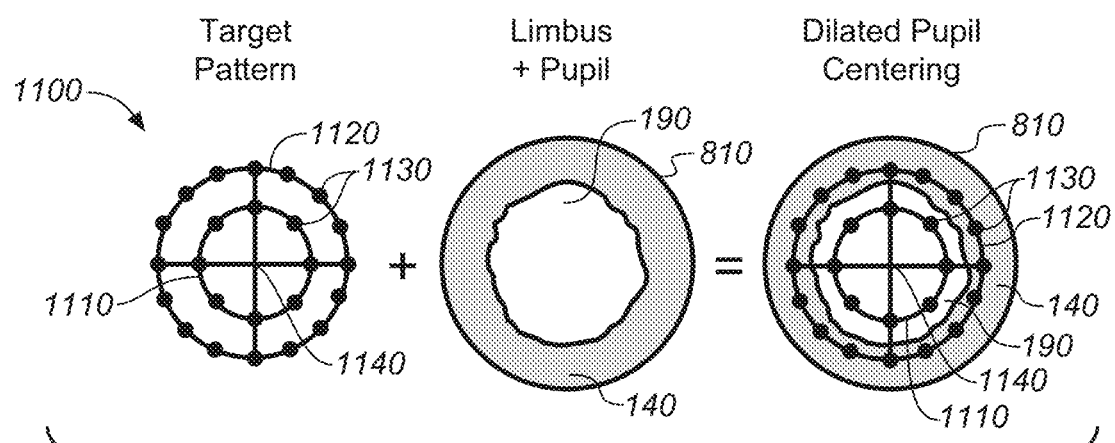

FIGS. 11A-11B each show a view of an eye including the limbus 810, iris 140, and pupil 190 onto which is projected an example visualization pattern 1100 comprising two concentric circles or closed curves 1110 and 1120 with dots 1130 on the curves and a cross hair 1140. The combination of lines and dots provides a pattern easily focused on the target tissue. The lines are produced by moving the visualization beam along the desired pattern. The dots are produced by dwelling the visualization beam for longer periods at the dot locations in the scan pattern. The dots may provide enhanced visualization on the target tissue because they are more intense than the lines. The inner circle or closed curve 1110 represents the size and location of the desired opening in the anterior capsulorrhexis. The outer circle 1120, which may be sized independently of the inner circle size, may be used to center the capsulorrhexis on the limbus as illustrated in FIG. 11A. Alternatively, the outside circle may be sized to facilitate centering on the interior boundary of the dilated pupil, as represented in FIG. 11B. The addition of the cross hair further enhances the ability to focus and center the visualization pattern.

FIGS. 12A-12L show additional visualization patterns each of which may comprise a combination of inner 1205, 1210 and outer 1220 closed curves, dots 1230 on the curves, dots 1230 not on curves, a cross-hair 1240, dashed arcs 1250, and/or straight-line segments 1260 forming closed curves. Generally, the closed visualization curves shown in these and other figures may be formed from straight line segments, which may be easier to program and/or easier to generate than curved arcs.

Figure 13A:
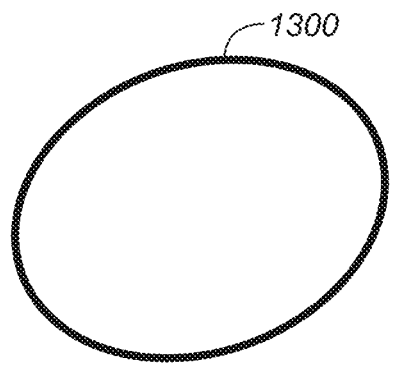
FIGS. 13A-13B show an example of an elliptical rhexis with a major and a minor axis and a rotation angle.
Figure 13B:
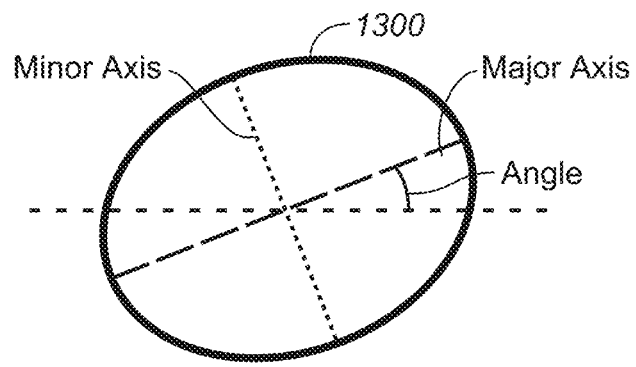
Figure 13C:
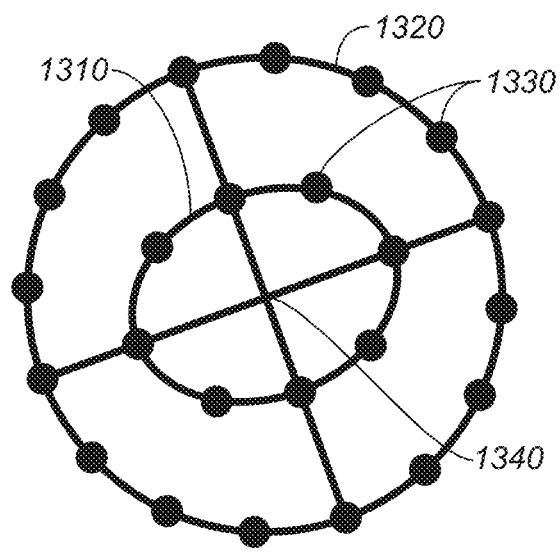
FIGS. 13C-13D show two examples of visualization patterns that may be used with the elliptical rhexis of FIGS. 13A-13B. Each pattern comprises a circular outer closed curve and an elliptical inner closed curve.
Figure 13D:
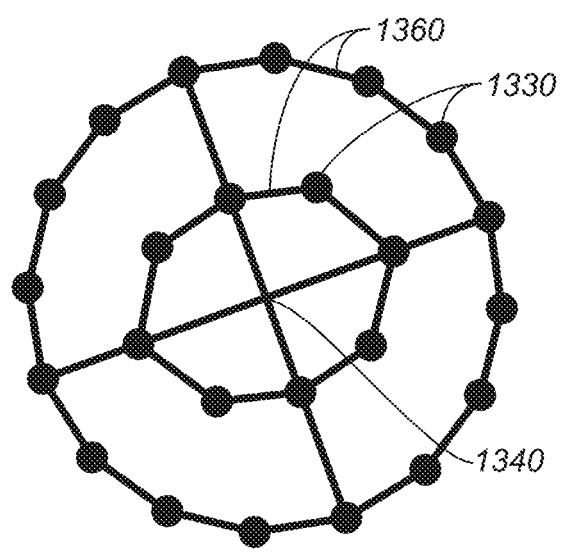

FIGS. 13A-13B show an example of an elliptical rhexis 1300 with a major and a minor axis and a rotation angle. FIGS. 13C-13D show two examples of visualization patterns that may be used with the elliptical rhexis of FIGS. 13A-13B. Each pattern comprises a circular outer closed curve and an elliptical inner closed curve (1320 and 1310, respectively, in FIG. 13C), dots 1330 on the curves, and a cross hair 1340. In FIG. 13D the closed curves are formed with straight-line segments 1360. The elliptical inner closed curves represent the size and location of the desired opening in the anterior capsulorrhexis. The outer circles, which may be sized independently of the inner ellipse size, may be used to center the capsulorrhexis on the limbus, for example.

Figure 14:
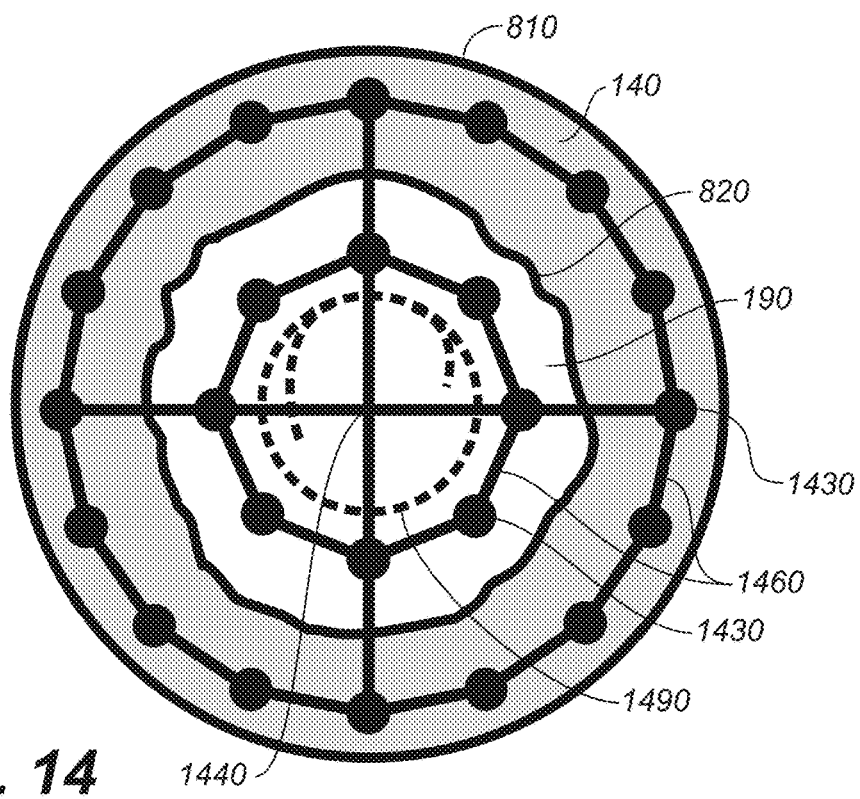
FIG. 14 shows a view of the eye with the limbus 810, iris 140, interior boundary of the iris 820, dilated pupil 190, a visualization pattern comprising a cross-hair 1440 and two circles 1460 with dots 1430 on the curves, and a treatment beam pattern for a circular rhexis 1490.

FIG. 14 shows a view of an eye including the limbus 810, iris 140, interior boundary of the iris 820, and pupil 190 onto which is projected an example visualization pattern comprising two concentric closed circles or curves with dots 1430 on the curves and a cross hair 1440. The closed curves are formed from straight-line segments 1460. The inner circle or closed curve represents the size and location of the desired opening in the anterior capsulorrhexis. The outer circle, which may be sized independently of the inner circle, may be used to center the capsulorrhexis on the limbus as illustrated. Alternatively, the outer circle may be sized to facilitate centering on the interior boundary of the dilated pupil. This figure also shows the treatment beam pattern 1490 for a desired circular rhexis. Treatment beam pattern 1490 differs from and is of a smaller diameter than the visualization pattern inner closed circle.

Figure 15:
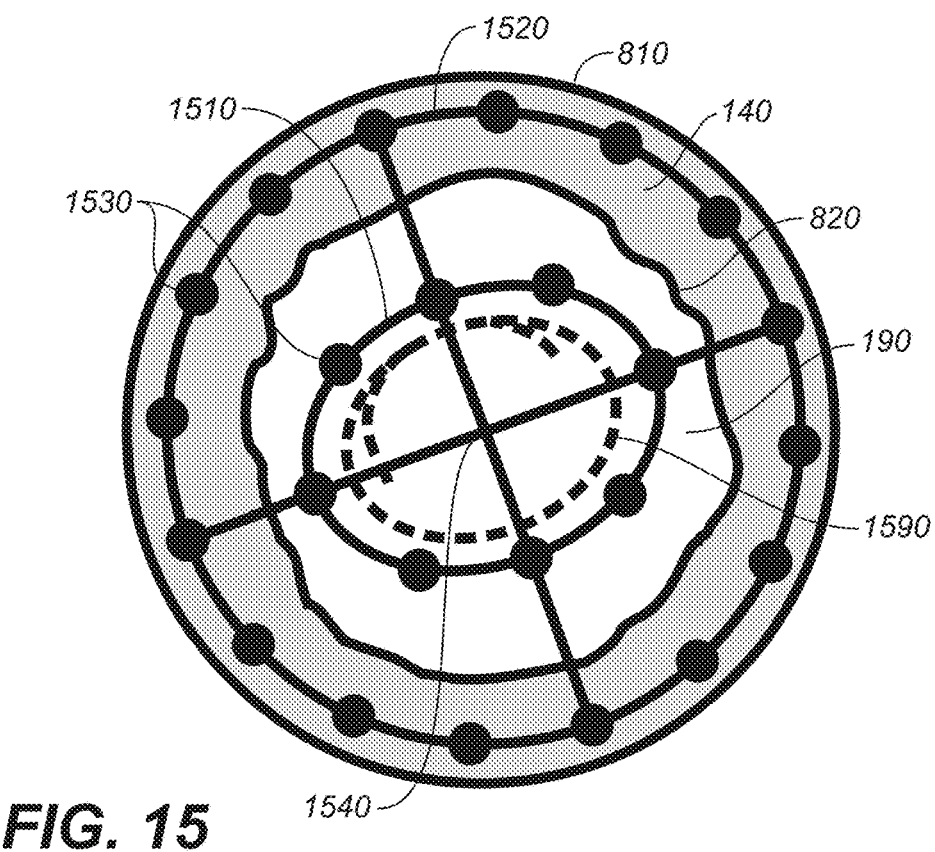
FIG. 15 shows a view of the eye with the limbus 810, iris 140, interior boundary of the iris 820, and dilated pupil 190, a visualization pattern comprising a cross-hair 1540 and outer circle 1520 with dots 1530, and an inner ellipse 1510 with dots 1530, and a treatment beam pattern for an elliptical rhexis 1590.

FIG. 15 shows a view of an eye including the limbus 810, iris 140, interior boundary of the iris 820, and pupil 190 onto which is projected an example visualization pattern comprising an outer circular closed curve 1520 and an inner elliptical closed curve 1510, dots 1530 on the curves, and a cross hair 1540. The elliptical inner closed curves represent the size and location of the desired opening in the anterior capsule. The outer circle, which may be sized independently of the inner ellipse, may be used to center the capsulorrhexis on the limbus as illustrated. Alternatively, the outer circle may be sized to facilitate centering on the interior boundary of the dilated pupil. This figure also shows the treatment beam pattern 1590 for a desired elliptical rhexis. Treatment beam pattern 1590 differs from and is smaller than the visualization pattern inner ellipse.

Any other suitable visualization beam patterns may also be used. One or more visualization beam pattern shapes may be preprogrammed into a laser capsulorrhexis device (described in more detail below) by the manufacturer, for example. At or prior to the time of treatment an operator may then, for example, select a pattern size and shape to be used to guide the treatment.

The location of the visual axis relative to center on the limbus or dilated pupil may also be measured on a separate diagnostic device. The offset data from center may then also be manually or automatically input into the laser capsulorrhexis device. In such cases, the visualization pattern may be arranged so that when an exterior portion of the visualization pattern (e.g., a circle) is positioned or centered on the eye anatomy of the limbus or dilated pupil, the center of an interior portion (e.g., a circle or ellipse) of the visualization pattern is offset from the center of the limbus or dilated pupil to lie on the visual axis. The center of the closed curve of the treatment pattern may be correspondingly offset from the center of the limbus or dilated pupil, so that the central circle or ellipse of the visualization pattern indicates the perimeter of the desired rhexis.

The visualization pattern laser beam may have any suitable wavelength in the visible spectrum. The visualization beam may be scanned across the tissue to be treated at, for example, a speed greater than about 450 mm/second, though it may also dwell to form dots or other brighter features in the visualization pattern. Any suitable scanning speeds may be used. The diameter of the visualization light beam on the tissue surface may be, for example, about 50 to about 600 microns. The visualization laser beam power at the tissue may be, for example, less than about 10 mW or less than about 1 mW when the beam is dwelling on a dot in the visualization pattern. When the visualization beam is scanning its power may be, for example, less than about 30 mW. Generally the power and the wavelength of the laser beam are selected to provide a sufficiently visible visualization pattern without significantly depleting any absorbing agent that has been deposited on the tissue to facilitate treatment.

Treatment Beam and Scanning Parameters

Generally, parameters characterizing the treatment laser beam and the treatment beam scanning procedure are selected to provide the desired laser induced thermal separation of tissue at the treated tissue while minimizing or reducing the risk of damage to the retina. These laser and scanning parameters may include, for example, laser wavelength, laser beam power, spot size at the treated tissue, fluence and peak irradiation at the treated tissue, spot size on the retina, fluence and peak irradiation on the retina, scanning speed, temporal profile of the laser beam during the scan, and scanning pattern size and location on the retina.

Typically, a treatment beam from a continuous wave laser traces the treatment beam pattern in a single pass in a time period of, for example, less than about 10 seconds, less than about 5 seconds, less than about 1 second, about 10 seconds, about 5 seconds, or about 1 second. The treatment beam may move across the treated tissue at a speed, for example, of about 20 millimeters/second (mm/s) for a 1 second scan to about 2 mm/s for a 10 second scan, but any suitable scanning speed and duration may be used. The formation of irregularities or tears in the resulting rim of tissue is reduced or avoided because movement of the continuous wave laser beam along the treatment path occurs during irradiation of the treated tissue (rather than between discrete laser pulses, for example), and thus all portions of the rim are formed with the same or similar irradiation and thermal conditions. Using a single pass of the treatment beam also helps to ensure completion of the capsulorrhexis even if there is slight movement of the eye relative to the trajectory.

In variations in which the treatment beam path begins on the interior of the closed curve of the treatment pattern (see FIG. 4C, for example), the initial scanning speed in the interior portion of the treatment path may be less than the scanning speed along the closed curve. The scanning speed on the interior portion may, for example, ramp up to the speed used along the closed curve. The average speed along the interior portion may be, for example, about ½ of the scanning speed used along the closed curve, or about ⅔ of the scanning speed used along the closed curve, or between about ½ and about ⅔ of the scanning speed used along the closed curve.

Figure 16:
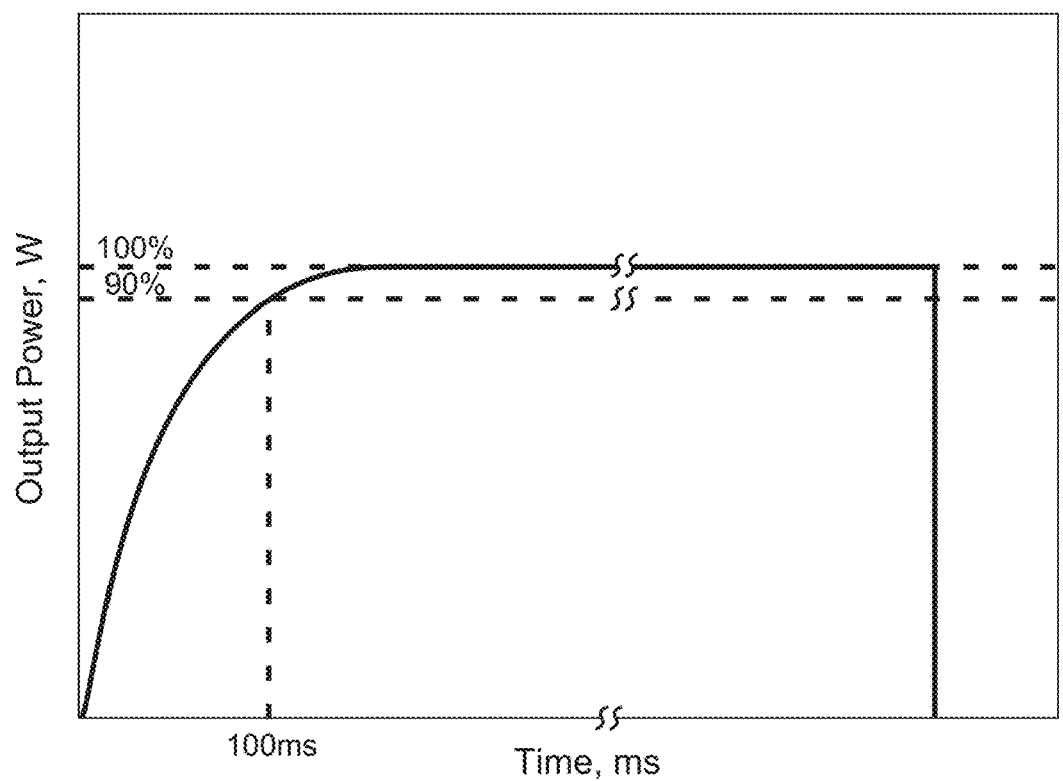
FIG. 16 shows a plot of power versus time for an example treatment laser output pulse delivered to the collagen containing tissue that may be used in the devices and methods described herein.

Referring now to the plot of laser power versus time shown in FIG. 16 for an example treatment beam scan, at the beginning of a treatment scan the power in the treatment beam may be ramped up slowly (and optionally monotonically, as shown, to be efficient with time). As noted above in the summary section, this slow ramp up may allow the tissue near the starting point of the pattern to initially stretch without separating, thereby reducing the shear stress/tension at the start of the pattern. This slow ramp up may also avoid or minimize local shock waves in the fluid adjacent to the target tissue that might otherwise be generated by a faster thermal turn-on. For example, the laser beam may ramp-up monotonically from zero to about 90% of full treatment power over a period of from about 5 milliseconds (ms) to about 200 ms, for example about 100 ms. This ramp-up of power typically occurs while the laser beam is scanned along an initial portion of the treatment path. In variations in which the treatment beam path begins on the interior of the closed curve of the treatment pattern (see again FIG. 4C, for example), the ramp-up in laser beam power may occur along the initial interior portion of the treatment path and be complete before the laser beam reaches the closed curve portion of the treatment pattern. In such variations the scanning speed of the beam along the initial interior portion of the treatment path may also ramp up to the speed used along the closed curve, as described above. The average speed along the interior portion of the path may be about 25% of the scanning speed used along the closed curve, for example.

As shown in FIG. 16, turn-off of the treatment laser beam pulse at the end of the treatment scan may be much more abrupt than turn-on.

As noted earlier in this specification, the treatment laser beam wavelength may be selected to be strongly absorbed by a light absorbing agent optionally added onto or into the tissue to be treated. The treatment laser may operate at a wavelength of about 577 nanometers, or about 590 nanometers, or about 810 nanometers, for example. In such examples the light absorbing agent, if used, may be Trypan Blue or Indocyanine Green, respectively. Alternatively, the treatment laser wavelength may be selected to be absorbed or strongly absorbed by the tissue itself. Any suitable wavelength for the treatment beam may be used.

As described in more detail below, typically the treatment laser beam is focused to a waist at or near the location of the tissue to be treated, and then expands in diameter as it propagates to the retina. Also, typically the scanning pattern is expanded on the retina compared to its size on the treated tissue. Consequently, parameters such as fluence and peak irradiation for the treatment beam may have different and larger values at the treated tissue compared to their values at the retina.

The methods and devices disclosed herein typically rely on laser induced thermal separation of tissue rather than on laser induced ablation, and may therefore use much lower treatment beam fluence and peak irradiation values at the treated tissue than typically required by other laser based surgical procedures. In addition, the methods and devices disclosed herein may use treatment laser beams having relatively high average power without producing peak irradiation values that are potentially damaging to the retina or other eye tissue, because these methods and devices may use long (e.g., 1 to 10 second) pulses from a continuous wave laser. In contrast, laser based surgical procedures using much shorter Q-switched or mode-locked laser pulses may be required to operate at much lower average powers to avoid potentially damaging peak irradiance values, which may increase the time required to provide a desired fluence.

The average power of the treatment beam, which is selected depending in part on the absorption strength of the absorbing agent at the treatment beam wavelength or the absorption strength of the treated tissue at the treatment beam wavelength, may be for example about 300 mW to about 3000 mW. Any suitable average power may be used.

The treatment beam fluence on a particular tissue depends on the average power in the treatment beam, the diameter of the treatment beam at that tissue, and the scanning speed of the treatment beam across that tissue. For the methods and devices disclosed herein, at the tissue to be treated (e.g., the anterior lens capsule) the treatment beam fluence for a 1 second scan may be for example about 80 Joules/centimeter$^2$ (J/cm$^2$) to about 450 J/cm$^2$. For a 5 second scan the fluence at the tissue to be treated may be for example about 100 J/cm$^2$ to about 1600 J/cm$^2$. For a 10 second scan the fluence at the tissue to be treated may be for example about 100 J/cm$^2$ to about 2000 J/cm$^2$.

The treatment beam peak irradiance on particular tissue depends on the peak power in the treatment beam and the diameter of the treatment beam at that tissue. For the methods and devices disclosed herein, at the tissue to be treated (e.g., the anterior lens capsule) the treatment beam peak irradiance may be, for example, less than about 2,000 Watt/centimeter$^2$ (W/cm$^2$), or less than about 5,000 Watt/centimeter$^2$ (W/cm$^2$), or less than about 10,000 W/cm$^2$, or less than about 100,000 W/cm$^2$, or less than about 200,000 W/cm$^2$. For example, in some variations the peak irradiance on the anterior lens capsule is about 2,100 W/cm$^2$ and the fluence at the anterior lens capsule is about 130 J/cm$^2$.

In general, at the retina the treatment beam fluence may be, for example, less than about 10 J/cm$^2$ and the irradiance may be, for example, less than about 400 milliwatts/cm$^2$ (mW/cm$^2$). In one embodiment with an NA of about 0.06 and a beam diameter of about 2000 microns on the retina, for a 1 second scan speed, the fluence at the retina may for example have a maximum of about 0.3 J/cm$^2$. For a 5 second scan the fluence at the retina may for example have a maximum of about 1.5 J/cm$^2$. For a 10 second scan the fluence at the retina may for example have a maximum of about 3.0 J/cm$^2$.

Figure 17:
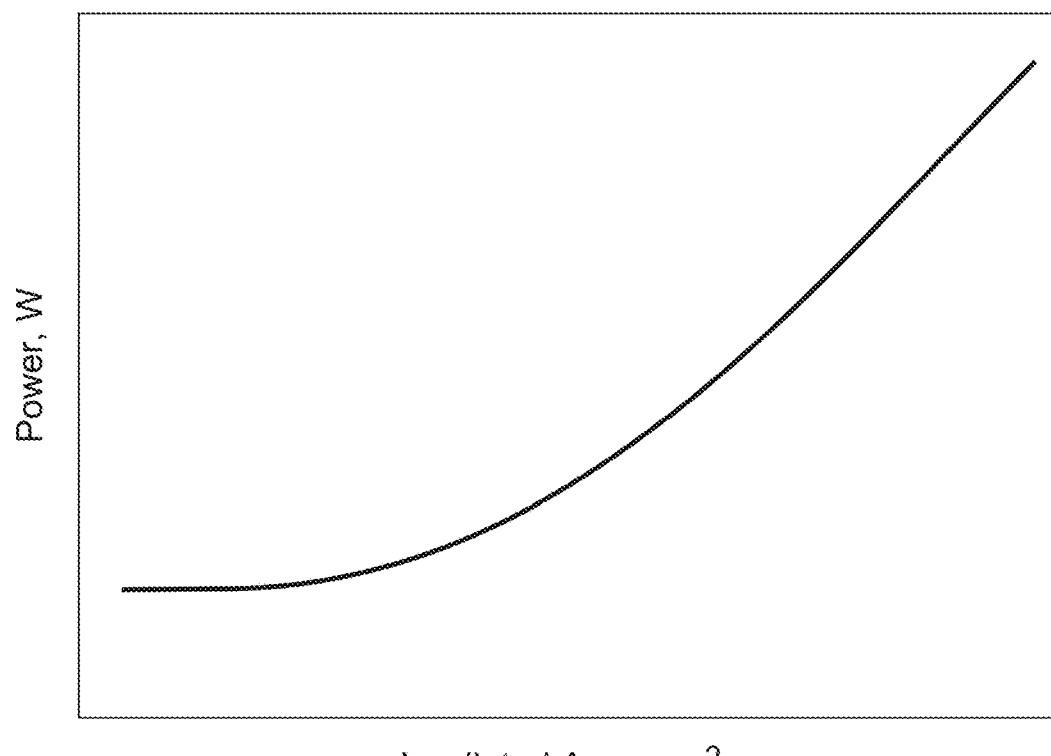
FIG. 17 illustrates the dependence of the power as a function of irradiated area required to achieve thermal separation of the anterior capsule in the eye. The power has a low dependence at the smaller areas, and as the area increases there is a greater dependence of power on the irradiated area.

Referring now to FIG. 17, the inventor has discovered that the minimum treatment laser beam power required for laser induced separation of tissue has a non-linear response to the irradiated beam area on the treated tissue. In particular, this plot demonstrates that there is a low dependence of the power required for tissue separation on the size of the irradiated area, specifically below a beam diameter of about 100 to about 200 microns. However, as the spot size increases far above a diameter of about 300 microns, more power is required to separate tissue.

Hence it may be preferable to use a treatment beam having a diameter of about 200 microns at the treated tissue. This may reduce the required irradiance in the treatment beam and thus decrease the risk of damaging the retina. More generally, the treatment laser beam may have a diameter of, for example, about 50 microns to about 400 microns at the treated tissue.

Use of Surgical Contact Lens

Figure 18A:
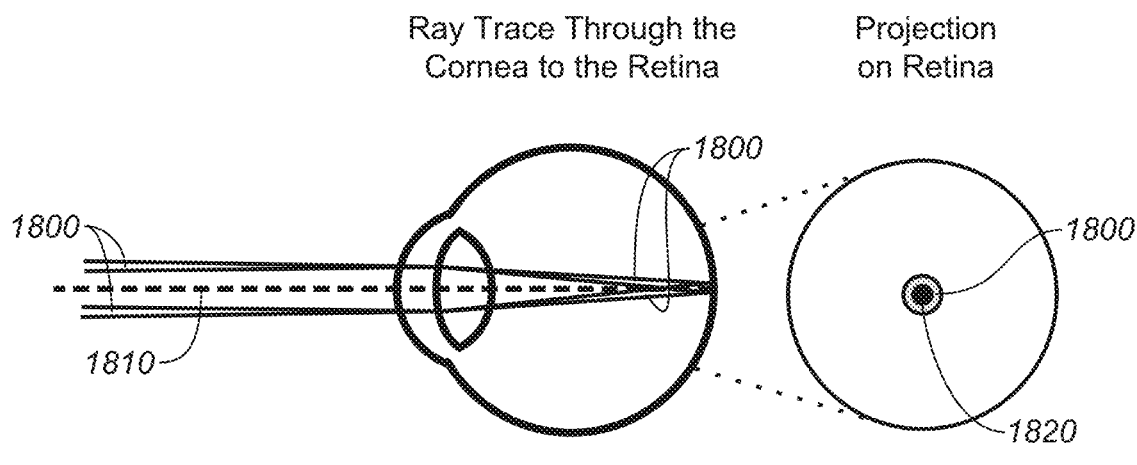
FIGS. 18A-18C show three example ray traces of a scanned laser beam directed into an eye through the cornea and the lens and onto the retina, and the resulting projection of the scanned laser beam on the retina.
Figure 18B:
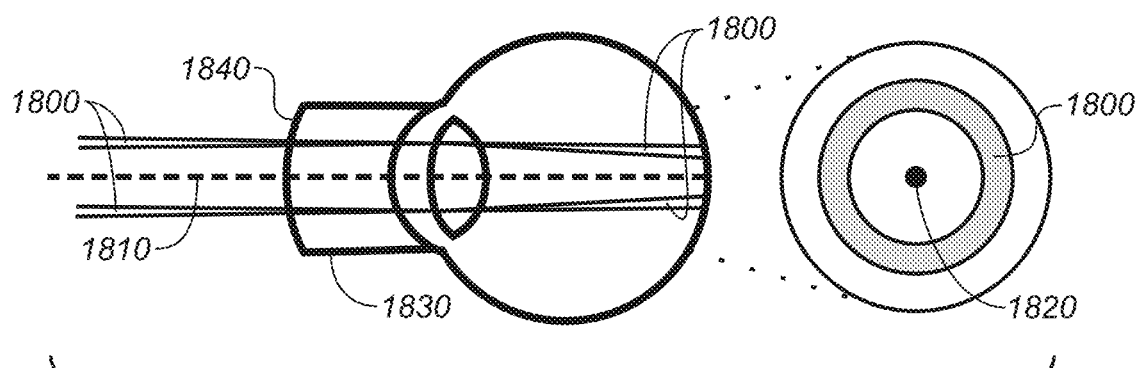
Figure 18C:
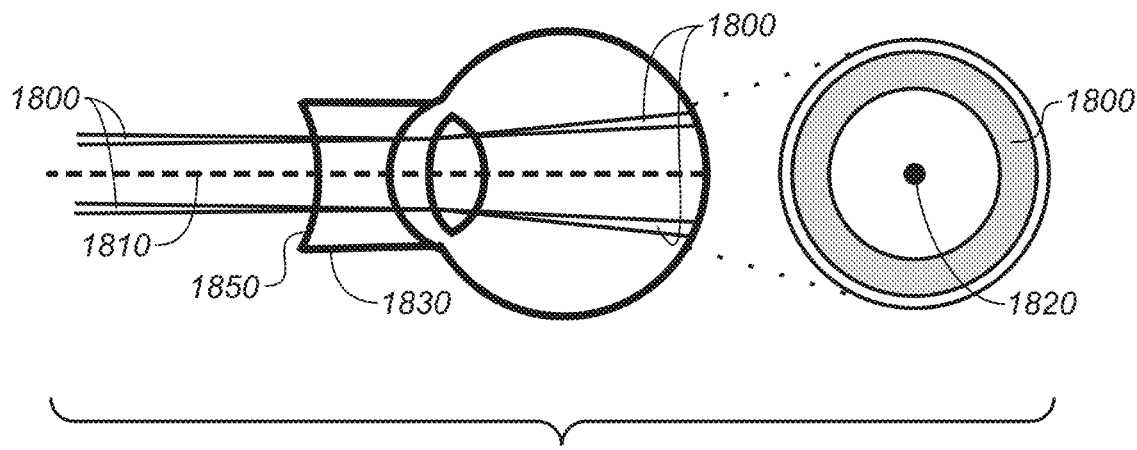

A surgical contact lens may be used to neutralize or approximately neutralize the cornea's focusing power on the retina to further reduce risk of damaging the retina, and in particular to protect the fovea. (The fovea is located in the center of the macula region of the retina, and is responsible for sharp central vision). FIG. 18A demonstrates that in the absence of a surgical contact lens, a scanned treatment laser beam pattern 1800 centered around the visual axis 1810 would be focused into the proximity of the fovea 1820 on the retina. It is likely that the fovea would be under constant irradiation for the full duration of the scanned pattern. FIG. 18B demonstrates that in the presence of a surgical contact lens 1830 with a mild convex anterior surface 1840 minimizing the majority of the corneal optical lens power, a scanned laser beam pattern 1800 centered around the visual axis 1810 may be projected onto the retina such that it avoids the fovea and instead surrounds the fovea. FIG. 18C demonstrates that in the presence of a surgical contact lens 1830 with a concave anterior surface 1850, a scanned laser beam pattern 1800 centered around the visual axis may be projected on to the retina so that it avoids the fovea and instead surrounds the fovea. Moreover, the trace of the laser beam projected on to the retina may be further refracted way from the fovea than would be the case for a convex surgical contact lens. In addition the area irradiated by the laser beam would be larger on the retina, which reduces the delivered laser energy per unit area (fluence) on the retina.

Use of a surgical contact lens as just described to refract the scanned treatment beam pattern away from the fovea allows the treatment laser to be operated at a higher power, without damaging the fovea or other portions of the retina, than might otherwise be the case. Such use of a surgical contact lens is optional, however.

Treatment/Scanning Device

Figure 19:
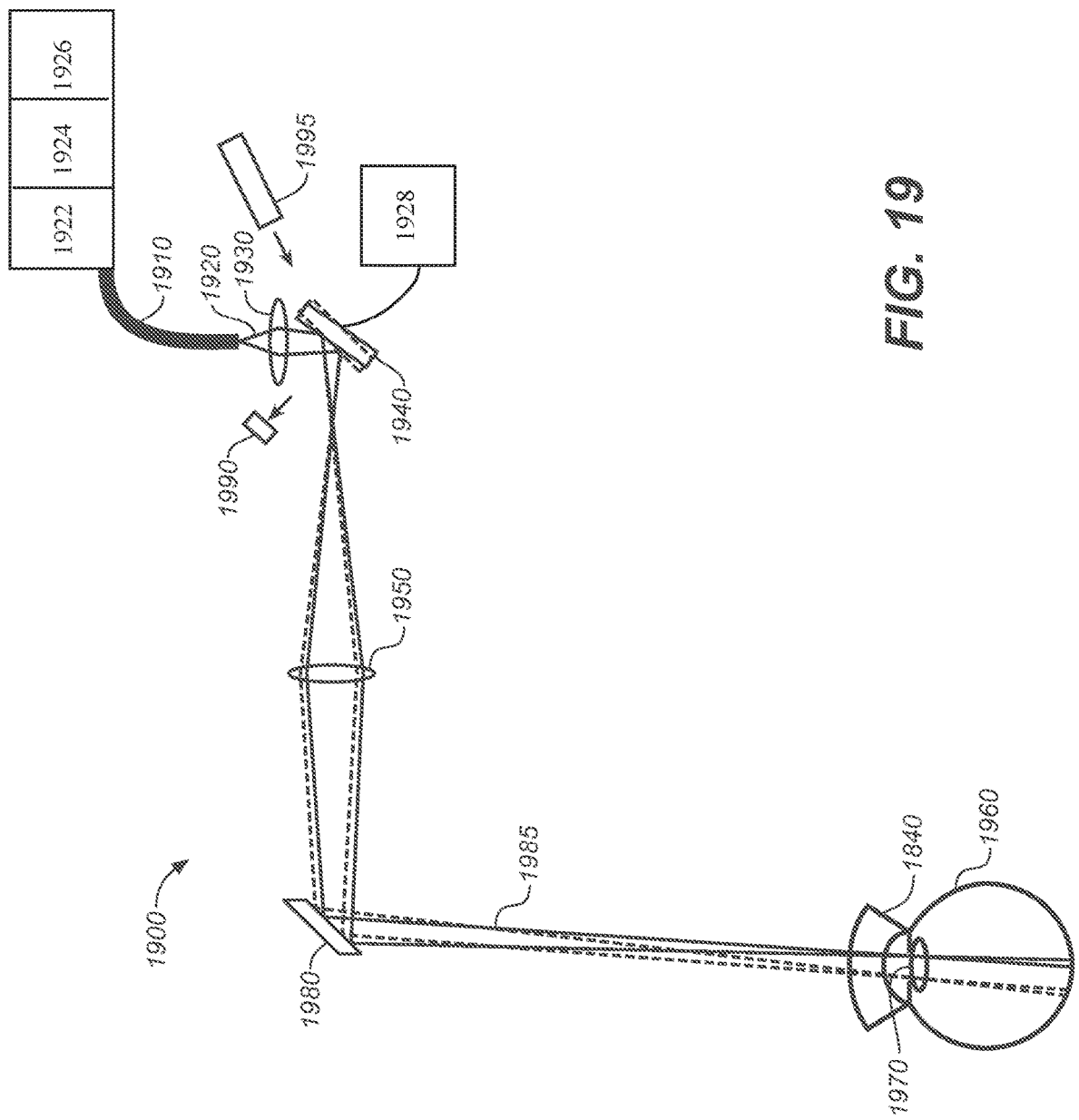
FIG. 19 shows elements of an example device that may be used to scan laser beams in an eye to perform ophthalmic surgeries as described herein.

Referring now to FIG. 19, an example device 1900 may be used to perform ophthalmic surgeries as described herein. FIG. 19 illustrates the optical beam focusing and the scanner optical properties of this device. Device 1900 comprises an optical fiber 1910 that delivers collinear visualization and treatment laser beams 1920 (e.g. from treatment laser 1922 and visualization laser 1924) to a lens 1930, which focuses the beams beyond a two-dimensional scanner 1940. The two-dimensional scanner 1940 scans the visualization or treatment laser beam to provide the desired visualization or treatment beam pattern. Lens 1950 focuses the treatment and visualization laser beams to a waist in the treated eye 1960 at or approximately at the anterior lens capsule 1970. After passing through that waist the laser beams expand and are thus defocused on the retina. Optional stationary final mirror 1980 may be used as shown to direct the beams to be collinear or nearly collinear with microscope optics (see FIGS. 20, 21, and 25).

The two-dimensional scanner 1940 has different tilt positions to create a scanned pattern on the anterior capsule. The solid line depiction of the scanner represents one example tilt position, and the dash line depiction of the scanner represents a second tilt position. In this example device the optics are designed such that there is a scanner pattern invariant 1985 (a location at which there is no apparent motion of the scanned pattern) and waist between the lens 1950 and its focus. Compared to a system lacking a scanner pattern invariant located in this manner, this arrangement has the advantages of reducing or minimizing the size of the optical device, reducing or minimizing the required two-dimensional scanner tilt, reducing or minimizing the area required on the optional final mirror, and providing additional divergence of the scanned pattern along the optical path so that for the same size and shape pattern on the anterior capsule, the projection on the retina has a larger diameter and therefore less fluence and less associated temperature rise at the retina.

Example device 1900 also includes an optional light detector 1990. The two-dimensional scanner 1940 may deflect the treatment or visualization laser beams to detector 1990, which may be used for example to measure their power. Detector 1990 may be a detector array, for example, in which case the two-dimensional scanner 1940 may scan the treatment or visualization laser beam across the detector array to confirm that the scanner is functioning properly.

Device 1900 further includes an optional aberrometer 1995, which may be used to make refractive measurements of the eye to be treated. This may be accomplished, for example, by tilting the two-dimensional scanner 1940 to direct an output light beam from aberrometer 1995 along the optical path used for the visualization and treatment beams into the eye. Alternatively, a light beam from aberrometer 1995 could optionally be introduced into the optical path of device 1900 with a dichroic beam splitter, for example.

Device 1900 includes a scanner controller 1928. The scanner controller may be preprogrammed with one or more treatment beam pattern shapes and one or more visualization pattern shapes by the manufacturer, for example. At or prior to the time of treatment an operator may then, for example, select treatment and visualization pattern sizes and shapes to be used in a particular treatment procedure.

Any other suitable device design may also be used to perform the procedures described herein.

Integration with Microscope

Figure 20:
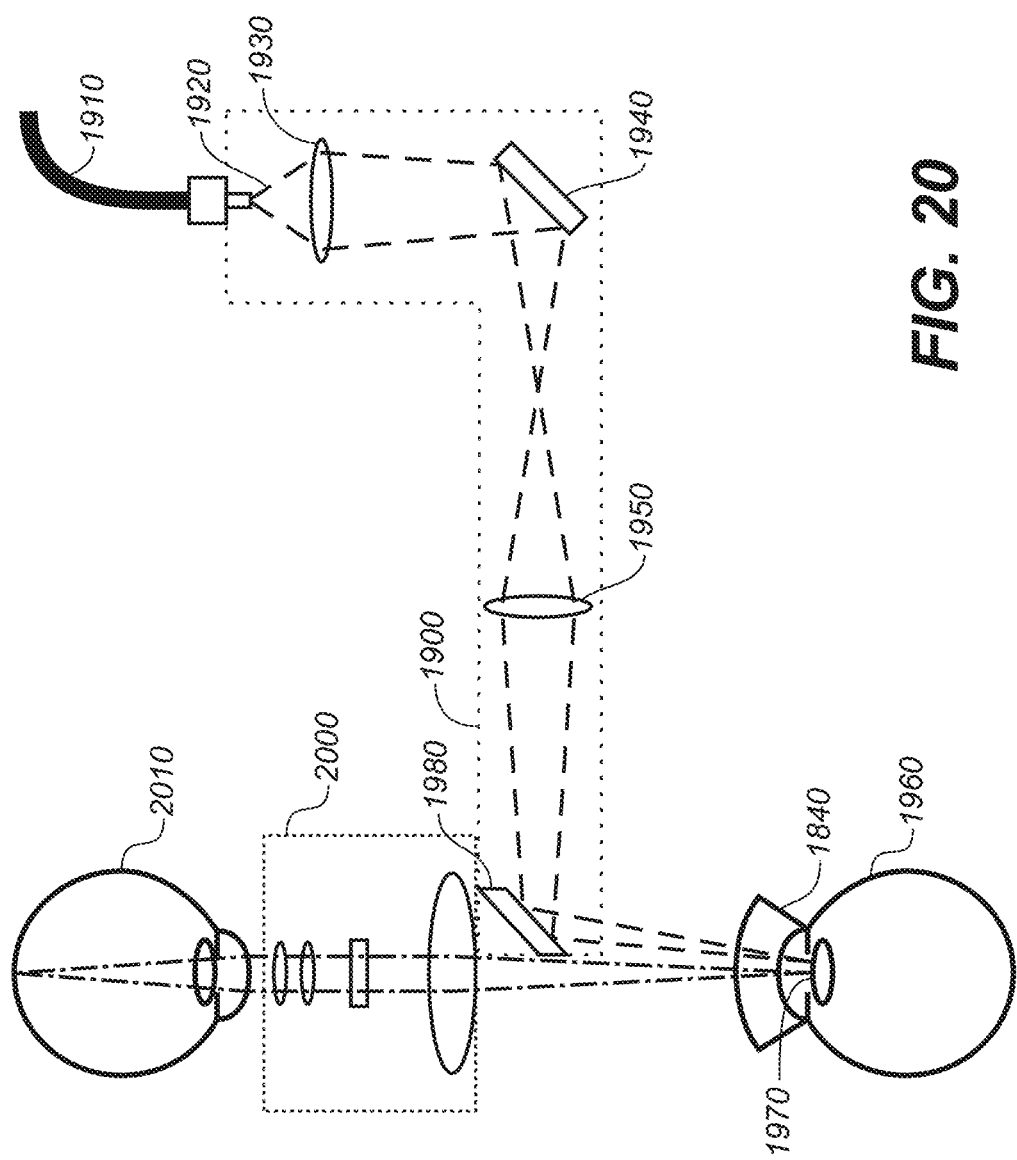
FIG. 20 shows the example device of FIG. 19 externally integrated with a microscope as an attachment to the microscope.

Example device 1900 described above may be integrated with a microscope. FIG. 20 shows an example in which device 1900 is externally integrated with a microscope 2000. The integration is external because device 1900 and microscope 2000 do not share any optical elements. Microscope 2000 may be used by a human operator 2010 (eye only shown) to observe the eye 1960 to be treated and the visualization pattern prior to, during, and after the treatment procedure.

Figure 21:
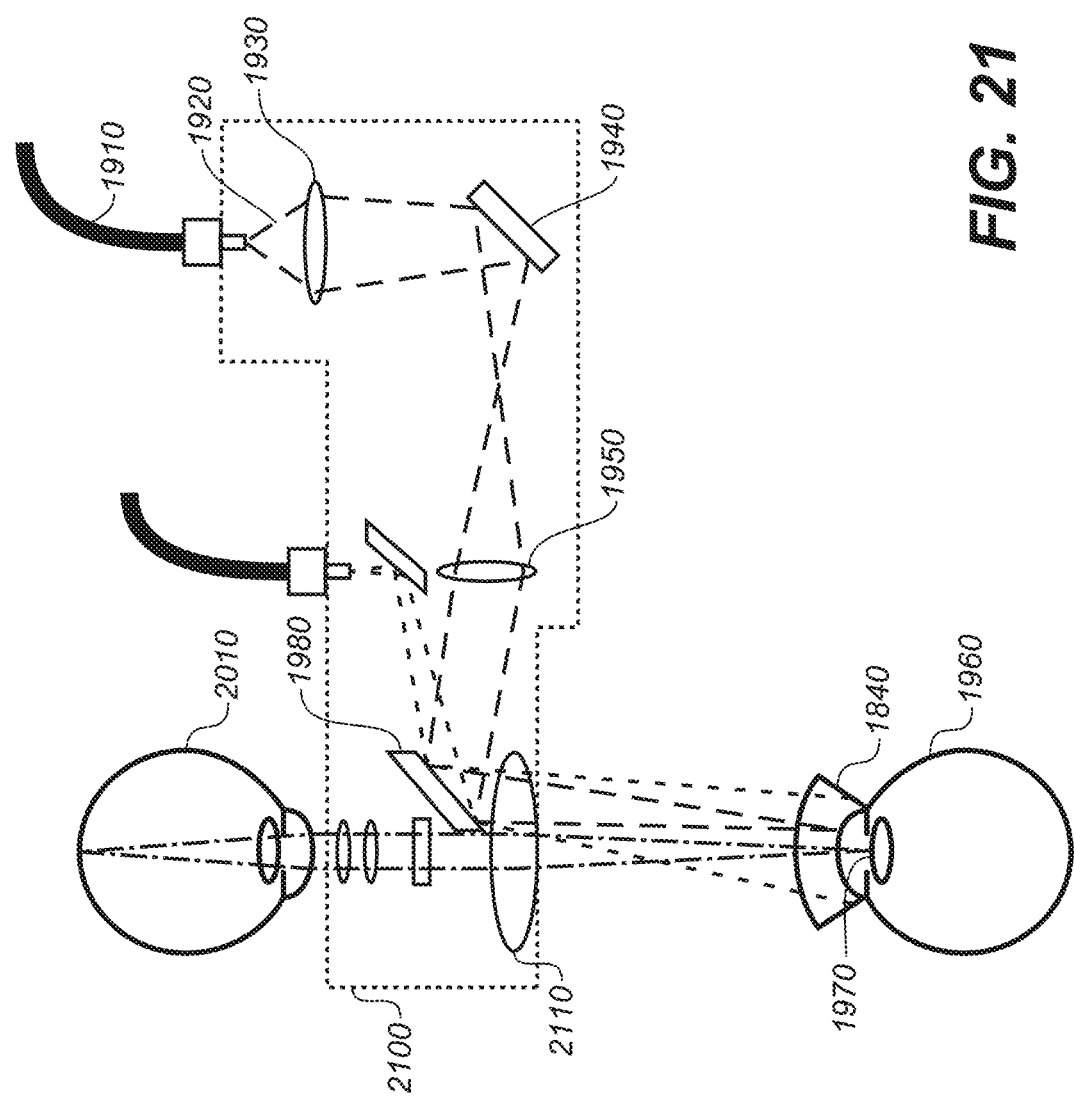
FIG. 21 shows the example device of FIG. 19 internally integrated with a microscope, with a shared illumination mirror and microscope objective.

FIG. 21 shows an example in which device 1900 of FIG. 19 is internally integrated with a microscope to provide an integrated device 2100. In this integrated device, the treatment and visualization beam paths pass through the microscope objective 2110, and illumination for the microscope is provided by light output from an optical fiber 2120 along a path that shares stationary mirror 1980 with the treatment and visualization beam paths.

Any other suitable integration with a microscope may also be used.

Depth Alignment

A preliminary step in using device 1900 is to adjust the position of the device, or of the optical elements within the device, with respect to the patient's eye so that the waist (focus) of the treatment beam is at or approximately at the tissue to be treated. This may be done, for example, by viewing a visualization pattern (e.g., as described above) that is projected onto the tissue to be treated and adjusting device 1900 to bring the visualization pattern into focus on the tissue. However, in this approach any uncorrected deficiency in the operator's vision (e.g., myopia) may affect the operator's judgment as to whether or not the visualization pattern is in focus on the tissue to be treated. This may result in an incorrect adjustment of the treatment device.

Figure 22:
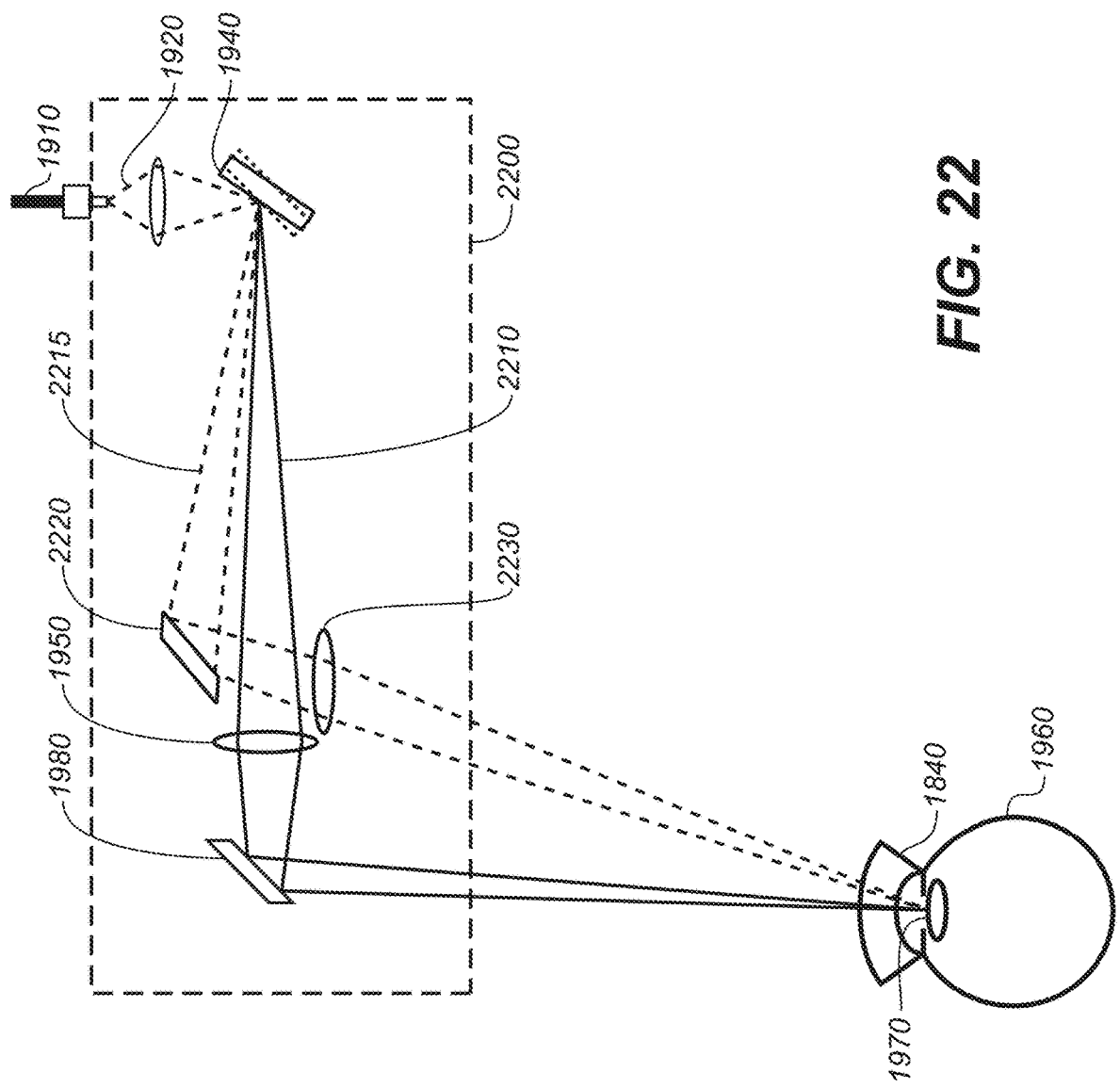
FIG. 22 shows another example device similar to that of FIG. 19 but also including optical elements facilitating depth alignment with respect to the tissue to be treated.

Referring now to FIG. 22, an example device 2200 for performing ophthalmic surgeries includes, in addition to the elements of device 1900 shown in FIG. 19, optical elements that produce a second visualization beam to facilitate depth alignment of the device. In particular, in a depth alignment mode, further described below, scanner 1940 in device 2200 dithers to direct a visible light visualization beam 1920 from optical fiber 1910 along two different optical paths to produce visualization beams 2210 and 2215. Scanner 1940 may dither between the two paths at a rate greater than or equal to about 30 Hertz, for example, so that flickering of the two beams is not typically noticeable to an operator.

Beam 2210 follows the optical path of the treatment and visualization laser beams described above with respect to FIG. 19, and may be scanned to produce any suitable pattern. Beam 2215 may also be scanned to produce any suitable pattern. Beam 2215 is directed to intersect beam 2210 at or approximately at the treatment beam waist. As further described below, the intersection of beams 2210 and 2215 may therefore be used to identify the location of the treatment beam waist and to determine whether or not the treatment beam waist is properly positioned at the tissue to be treated. In the illustrated example, beam 2215 is directed to intersect beam 2210 using mirror 2220 and lens 2230 but any other suitable optical arrangement producing the desired intersection may also be used. Lens 2230 typically focuses beam 2215 to a tight waist at the intersection of the two beams, to identify the location of that intersection with greater precision.

If the intersection of beams 2210 and 2215 (and thus the treatment beam waist) is not properly positioned at the treatment tissue, the position of device 2200 or of optical elements within the device may be adjusted with respect to the patient's eye to move the intersection of the visualization beams, and thus the treatment beam waist, to the desired position.

Referring now to FIGS. 23A-23C, in some variations beam 2210 is scanned to produce a line 2310 and beam 2215 is not scanned but instead focused to a tight waist that appears as a dot 2315 in these figures. Device 2200 is aligned (e.g., by the manufacturer) so that beams 2210 and 2215 intersect at or approximately at the location of the waist of the treatment beam, with the dot 2315 centered or approximately centered on line 2310. FIGS. 23A-23C show a view through a microscope (e.g., microscope 2000 of FIG. 20) of the tissue to be treated (e.g., the lens capsule). When the intersection of visualization beams 2210 and 2215 is not positioned at or approximately at the tissue to be treated, dot 2315 and line 2310 will appear to be displaced from each other as shown in FIGS. 23A-23B. Further, an operator may be able to determine whether the visualization beams intersect in front of or behind the tissue to be treated based on which side of line 2310 the dot 2315 appears to be located. After device 2200 is adjusted to position the intersection of beams 2210 and 2215 (and therefore the waist of the treatment beam) at or approximately at the tissue to be treated, line 2310 and dot 2315 will appear superimposed as shown in FIG. 23C.

Although the illustrated example uses a line 2310 and a dot 2315, any other suitable patterns for intersecting beams 2210 and 2215 may be used to identify and adjust the position of the treatment beam waist with respect to the tissue to be treated. Typically the visualization patterns used in depth alignment mode differ from those described earlier in this specification. Although in the illustrated example intersecting beams 2210 and 2215 are produced from a single visualization laser beam by dithering the scanner 1940, any other suitable method of intersecting visible beams to identify the location of the treatment beam waist may also be used. Beams 2210 and 2215 may have the same wavelength, as in the example just described, or different wavelengths.

Device 2200 may be switchable between several different operating modes including the depth alignment mode just described. For example, in some variations device 2200 may be switchable between at least the following modes:

Standby Mode: The treatment beam and all visualization beams are off.

Depth Alignment Mode: As described above, intersecting visualization beams are used to facilitate adjusting the position of the focus of the treatment beam optical system with respect to the position of the tissue to be treated. The treatment beam is not activated.

Ready Mode: Visualization patterns are projected onto the lens capsule to guide the treatment. The visualization patterns may facilitate alignment of the treatment beam with respect to anatomy of the eye, and/or indicate the desired perimeter of a rhexis to be produced with the treatment beam.

Fire Mode: Treatment laser beam emission is activated and incident on the tissue to be treated.

Referring to FIG. 24A, some variations of device 2200 may include a foot-operable control 2400 in which a first button 2405, located on top of shroud 2410 for example, may be activated to switch from Standby to Depth Alignment Mode, with the device remaining in Depth Alignment Mode. Button 2405 may be activated again to switch from Depth Alignment Mode to Ready Mode, with the device remaining in Ready Mode. While the device is in Ready Mode, a shrouded fire button 2415 may be activated to switch from Ready Mode to Fire Mode, activating the treatment beam and the treatment beam scan, after which the device returns to Standby Mode. Alternatively, button 2405 may be activated again to switch from Ready Mode to Standby Mode.

Some variations of device 2220 may also be switchable into and out of a Visualization Sizing Mode. In the Visualization Sizing Mode, a visualization sizing pattern is projected onto the anterior lens capsule to guide positioning of the desired rhexis and thus positioning of the desired closed curve of the treatment beam. The size (e.g., diameter or another dimension) of the visualization sizing pattern is adjustable to increase or decrease a corresponding dimension of the desired rhexis to be formed by the treatment beam. In these variations, the device may be switched between modes in the following order, for example: Standby Mode, Depth Alignment Mode, Visualization Sizing Mode, Ready Mode, Standby Mode. This may be done, for example, by sequential activation of button 2405 (FIG. 24A) as described above. The visualization sizing pattern projected during Visualization Sizing Mode may have the same geometry as the visualization pattern projected in Ready Mode, or be different. It may be advantageous for the visualization sizing pattern to differ in geometry from the visualization pattern, to make it easier for an operator to recognize in which mode the device is in.

Referring to FIG. 24B, foot operable control 2400 may further include buttons 2420A and 2420B, located on interior or exterior side walls of the shroud for example, that may be used to increase or decrease the size of the visualization pattern projected during Visualization Sizing Mode (and correspondingly increase or decrease the desired radius or another dimension of the rhexis to be formed by the treatment beam).

Any other suitable switching mechanism may be used to switch between the operating modes just described. The switching mechanism may be or include switches intended to be hand operated, for example. Further, variations of foot-operable control 2400 described above, or of any other suitable switching mechanism, may be configured to allow the device to be switched from Depth Alignment Mode to Standby Mode, from Visualization Sizing Mode (if available) to Depth Alignment Mode, or from Ready Mode to Visualization Sizing Mode (if available) or Depth Alignment Mode. This may be accomplished using additional switching buttons for these transitions, for example, or with a button that reverses the direction in which button 2405 moves the device through the sequence of modes.

Virtual Visualization Patterns

As described above, visualization patterns may be projected onto the anterior lens capsule with one or more scanned visualization laser beams to aid in the ophthalmic surgical procedure. As an alternative to such projected visualization patterns, virtual visualization patterns may be presented on a display and overlaid with a view of the anterior lens capsule to aid in the surgical procedure. These patterns are virtual in that they are presented as simulated images on the display but not actually projected onto the anterior lens capsule. Any of the visualization patterns described above, and any other suitable visualization patterns, may be presented as virtual visualization patterns in this manner. Such virtual visualization patterns may be used for any of the purposes described above with respect to projected visualization patterns. The Ready Mode of operation and the optional Visualization Sizing Mode of operation described above may employ virtual visualization patterns rather than projected visualization patterns, for example. Consequently, variations of the treatment devices described herein may employ treatment laser beams but lack the collinear visualization laser beam described with respect to FIG. 19, for example.

Figure 25:
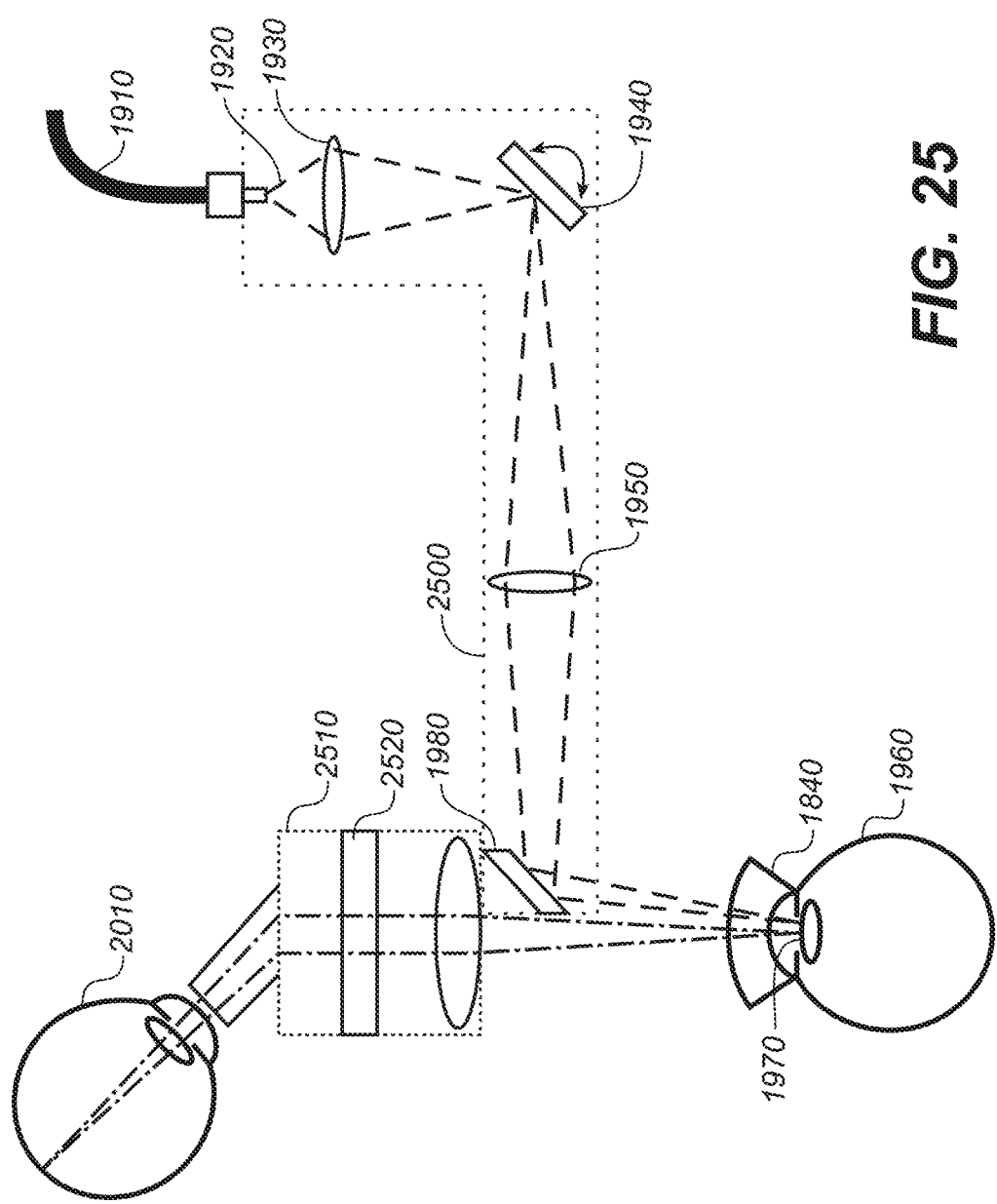
FIG. 25 shows an example device that may be used to scan laser beams in an eye to perform ophthalmic surgery, similar to the devices of FIGS. 19-22, with the device externally integrated with a microscope having a display on which a virtual visualization pattern may be overlaid with a view through the microscope of the surgical field.

For example, FIG. 25 shows a laser scanning treatment device 2500 similar to that of FIG. 19 externally integrated with a microscope 2510. Microscope 2510 includes a heads-up display 2520 on which a virtual visualization pattern may be overlaid with a view through the microscope of the surgical field to which a treatment beam 1920 is directed. Device 2500 may optionally provide a visualization beam collinearly with treatment beam 1920 to also provide a projected visualization pattern, but that is not necessary. Device 2500 may be internally integrated with a microscope employing a heads-up display to present virtual visualization patterns overlaid with the surgical field, rather than externally integrated as shown in FIG. 25. Such internal integration may be done similarly to as shown in FIG. 22, for example. In addition to displaying one or more virtual visualization patterns overlaid with the surgical field, heads-up display 2520 may display data or parameters relating to the surgical procedure. For example, the display may report the size or diameter of the rhexis to which the displayed virtual visualization pattern corresponds and/or the current mode of operation of the treatment device (e.g., Standby, Depth Alignment, Visualization Sizing, Ready, Fire, as described above).

Determining the Visual Axis

Typically, it is desirable to center the rhexis on the visual axis of the eye. Referring for example to FIGS. 19-22 and 25, the visual axis may be determined during an ophthalmic surgical procedure by directing a low power visible laser beam 1920 to the eye and having the patient fixate on the beam (look directly into it). When the patient is fixated on the laser beam, the laser beam is collinear with the visual axis of the patient's eye. Laser beam 1920 may be the treatment beam at low power, for example, a visualization laser beam, or another low power visible laser beam. The laser beam may be made to blink at a frequency perceptible by the patient, for example at less than about 30 Hertz, to may make it easier for the patient to fixate on it. The blinking rate may be varied, randomly for example, to further facilitate the patient fixating on the beam.

Such a blinking laser beam 1920 may be directed to the eye along or approximately along the optical axis of a microscope used in the ophthalmic surgical procedure (e.g., as in FIGS. 20-22 and 25) so that the location of the visual axis in the surgical field may be viewed through the microscope by an operator and/or with a camera (not shown). The offset of the visual axis from the center of the limbus or dilated pupil may thereby be measured, if desired. If virtual visualization patterns are being used on a heads-up display, as described above, they and the corresponding treatment beam path may be adjusted to center the rhexis on the visual axis or otherwise adjust the location and/or orientation of the rhexis with respect to the visual axis. If visualization patterns are instead being projected onto the anterior lens capsule with a scanning visualization beam, they and the corresponding treatment beam path may by similarly adjusted with respect to the visual axis.

Orientation of a Toric IOL

A toric IOL has a different optical power and focal length along two perpendicular axes. Toric IOLs are typically implanted with a preferred orientation that compensates for astigmatism or other optical aberrations in the eye. Proper orientation of a toric IOL may be determined using a (optionally blinking) laser beam on which the patient is fixated, as described above, by viewing a reflection of the laser beam from the back of the eye (e.g., the retina) after it has passed back through the toric IOL. The reflection may be viewed through a microscope (as in FIGS. 20-22 and 25, for example), either directly by an observer or with a camera (not shown). If the toric IOL orientation is not correct, the reflection from the back of the eye as viewed through the toric will be weak and have an elliptical shape. If the toric IOL orientation is correct, the reflection from the back of the eye will be stronger and will appear as a smaller and rounder spot.

The view of the reflection of the laser beam from the back of the eye may be enhanced by using a linearly polarized laser beam and viewing the reflection from the back of the eye through a crossed polarizer. Reflections of the laser beam from front surfaces of the eye (e.g., the cornea) and from the IOL will tend to retain the linear polarization of the incident laser beam. The reflection from the back of the eye, which may be better described as scattered rather than reflected light, will be less polarized than the incident laser beam. The crossed polarizer will therefore tend to reject a substantial portion of the reflections from the front surfaces of the eye and from the IOL, but pass a substantial portion of the light reflected or scattered from the back of the eye.

Eye Tracking

The position of the pupil or other features of the eye may be tracked with the devices and methods described above by imaging the eye under infrared illumination with a camera. Changes in the eye position during the ophthalmic surgery (before or during use of the treatment laser beam) may be fed back to a control system for the scanning laser treatment device to adjust the aim of the treatment laser accordingly.

Detecting a Light Absorbing Agent

In variations of the procedures described herein in which a light absorbing agent is used to facilitate laser assisted thermal tissue separation to create an opening in an anterior lens capsule, it may be desirable to optically or visually confirm that the light absorbing agent has been correctly placed prior to performing the treatment. In particular, it may be desirable to confirm that sufficient light absorbing agent is present on or in the capsule to prevent transmission of the treatment beam through the capsule at levels that might damage the retina or other portions of the eye interior. It may also be desirable to confirm that sufficient light absorbing agent is present on or in the capsule to result in complete thermal separation of the capsule along the treatment beam path.

Unsafe transmission of the treatment beam through the capsule might potentially occur if the treatment beam intensity incident on the treated tissue is above a predetermined threshold deemed safe for the retina and, for the speed (dwell time) at which the treatment beam is scanned on the treated tissue, there is insufficient light absorbing agent present in the treated tissue to absorb sufficient treatment beam light to reduce the treatment beam intensity transmitted through the treated tissue to below the safety threshold. Unsafe transmission of the treatment beam through the capsule might also potentially occur if the treatment beam intensity incident on the treated tissue is above the predetermined threshold deemed safe for the retina and the treatment beam intensity and scanning speed result in thermal tissue separation occurring or reaching completion at a location on which the treatment beam is still incident. Preferably, thermal tissue separation occurs or reaches completion at a particular location on the treatment beam path after the treatment beam has scanned past that location.

Unsafe transmission of the treatment beam through the capsule may be prevented, for example, by placing a sufficient amount of light absorbing agent on the tissue to be treated, selecting the treatment beam scanning speed to be sufficiently fast, and/or selecting the treatment beam intensity (determined by power and spot size) incident on the treated tissue to be sufficiently low.

Figure 26A:
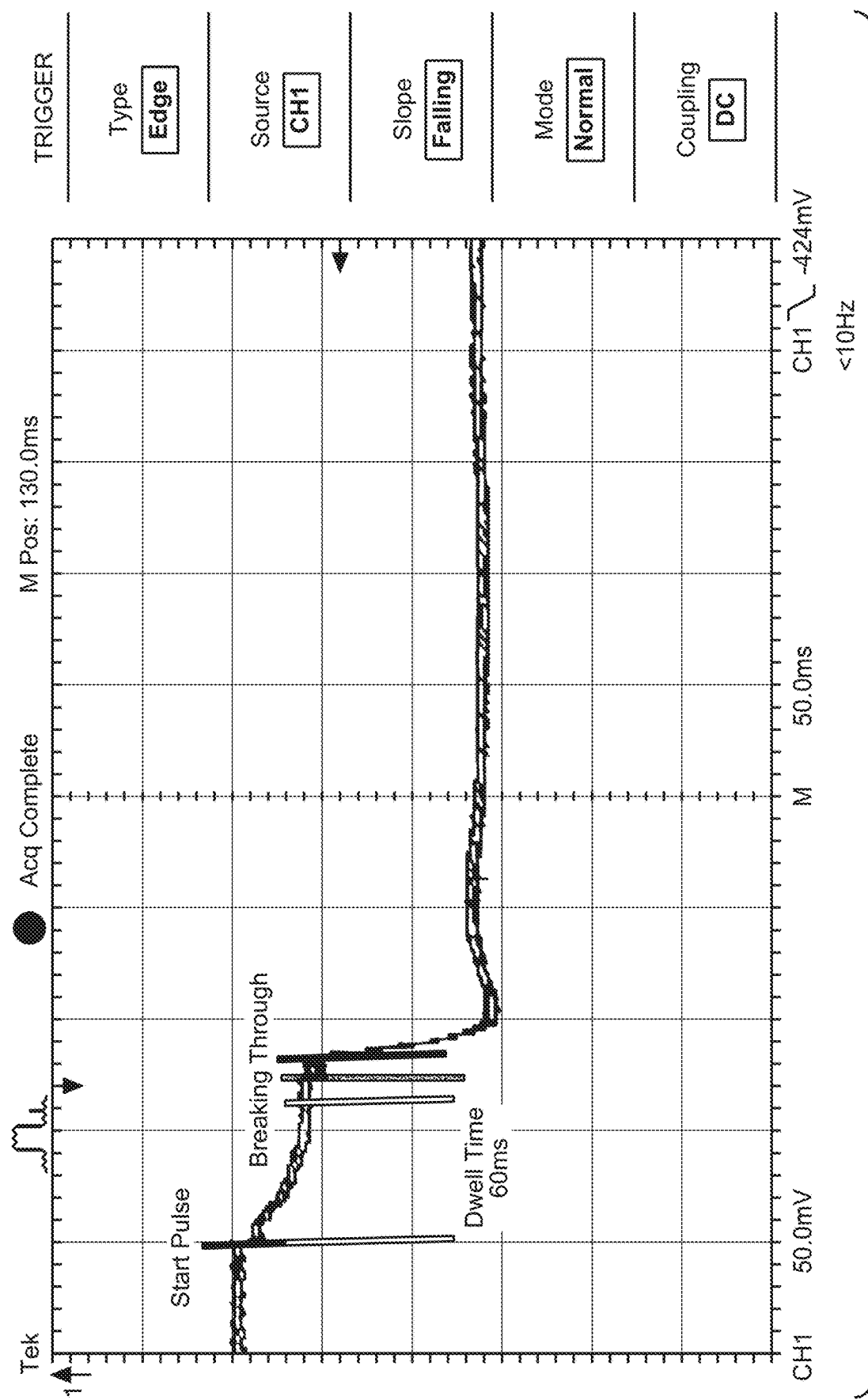
FIG. 26A shows an oscilloscope trace for a measurement of the transmission of a treatment laser beam, as a function of time, through an anterior lens capsule treated with a light absorbing agent.
Figure 26B:
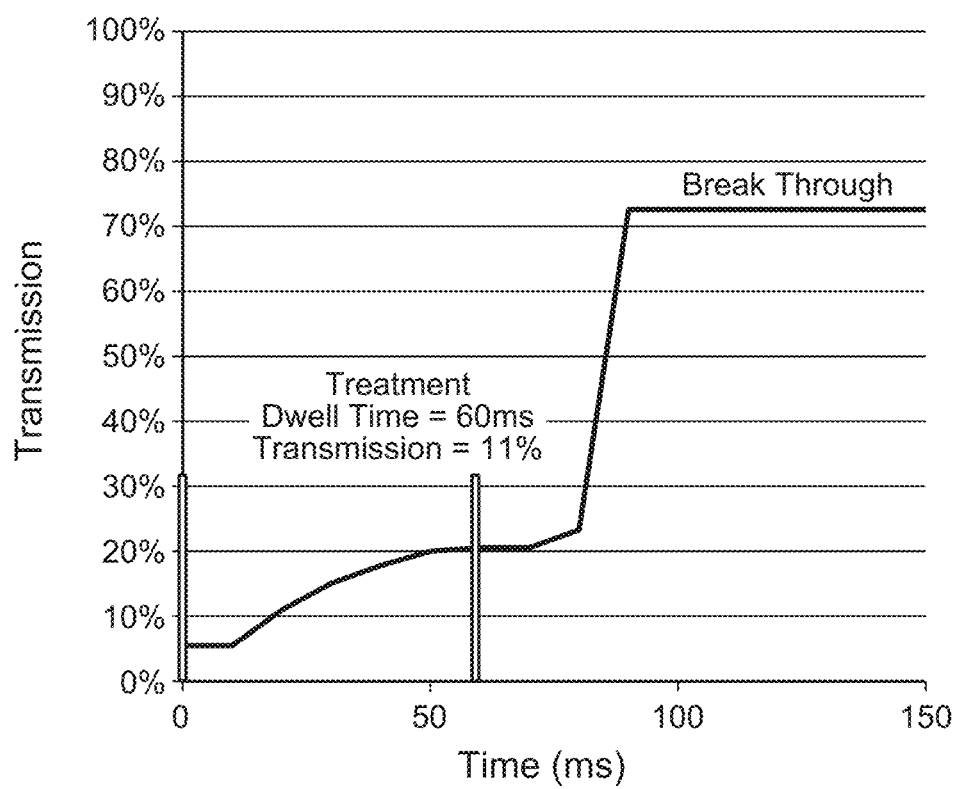
FIG. 26B shows the data of FIG. 26A presented in a plot of transmission versus time.

For example, FIG. 26A shows an oscilloscope trace for a measurement in which a laser beam having a wavelength of about 577 nanometers and a power suitable for a treatment beam is focused to a stationary spot having a diameter of about 200 microns on an anterior lens capsule (from a cadaver) for about 450 milliseconds. The anterior lens capsule has been treated with the light absorbing agent Trypan Blue. The horizontal axis of the oscilloscope trace represents time and the vertical axis represents transmission of the treatment beam through the capsule, with transmission increasing in the downward direction along the vertical axis. For clarity, the data of FIG. 26A are also presented in the transmission versus time plot of FIG. 26B with transmission increasing in the upward direction along the vertical axis.

As these figures show, under the conditions of this measurement the transmission of the treatment beam through the lens capsule initially slowly increases with time and then levels out at about 20%, followed by a sudden transition (breakthrough) to a much higher transmission that occurs at about 80 milliseconds. A scanning treatment beam with the same wavelength, power, and spot size might have a dwell time at any given location on the treatment beam path of less than or equal to about 60 milliseconds, for example, in which case "breakthrough" would not occur during scanning.

The quantity of the light absorbing agent present on or in the lens capsule may be assessed, for example, by measuring the reflection of broad band (e.g., white) light from the lens capsule and (optionally) the iris, the scleral regions, and/or a surgical contact lens. The broad band light may be provided, for example, using conventional microscope illumination in combination with a microscope integrated with the treatment devices described above, and the intensity of the reflection of the broad band light may be measured, for example, with a conventional still or video camera integrated with the microscope. Images of the reflected light may be analyzed, for example, with a conventional computer. Additionally, or alternatively, the light absorbing agent may be assessed by similarly measuring the intensity of the reflection of a narrow band detection laser beam from the lens capsule and (optionally) the iris, the scleral regions, and/or a surgical contact lens. In treatment devices described above, the detection laser beam (e.g. from detection laser 1926 in FIG. 19) may be provided through the same optical fiber that delivers the treatment and visualization beams, for example. The visualization pattern laser may provide the detection laser beam, for example. A detection laser may, for example, be scanned along the treatment path to determine the presence and quantity of light absorbing agent on the treatment path.

Depending on the wavelength at which the reflectance measurement is made, the light absorbing agent when present in or on the capsule may affect reflection from the capsule either by absorbing light and thus decreasing reflection from the capsule, or by reflecting light more strongly than the capsule tissue and thus increasing reflection from the capsule. (The light absorbing agent is more strongly absorbing than the capsule tissue at the treatment wavelength, but may be more reflective than the capsule tissue at other wavelengths). In either case, reflection measurements may be used to assess the amount of light absorbing agent present on or in the capsule.

The reflection measurements may be made both before and after introduction of the light absorbing agent to the lens capsule. As further discussed below, this may allow determination of a background-corrected relative reflectance resulting from the light absorbing agent, for example by determining the difference between the intensities of the reflections from the capsule measured before and after the light absorbing agent has been applied to the capsule. Typically, the light absorbing agent is not applied to the iris, the scleral regions, and any surgical contact lens used and thus should not affect reflection from the iris, the scleral regions, and the surgical contact lens. Consequently, as further discussed below, the reflections from the iris, the scleral regions, and the surgical contact lens measured before and after application of the light absorbing agent to the capsule may be used to adjust (e.g., normalize, scale, or background correct) the reflection intensities from the capsule. These adjustments may compensate, for example, for small changes in orientation of the eye occurring between the "before" and "after" measurements or for other differences in the reflection measurements unrelated to application of the light absorbing agent. The "before" and "after"

measurements of the intensities of the reflections from the iris, the scleral regions, and the surgical contact lens may also allow the absolute reflectance resulting from the light absorbing agent on or in the capsule to be determined.

Figure 27A:
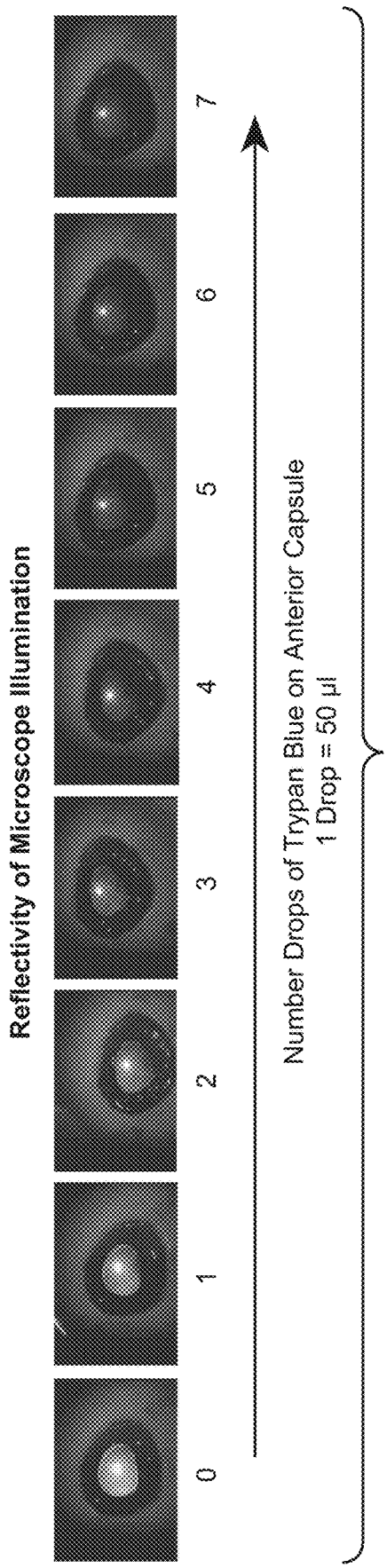
FIG. 27A and FIG. 27B show, respectively, example images and a plot of relative reflectance that illustrate decreasing reflectance of broad band illumination from a lens capsule as the amount of a light absorbing agent applied to the capsule is increased.
Figure 27B:
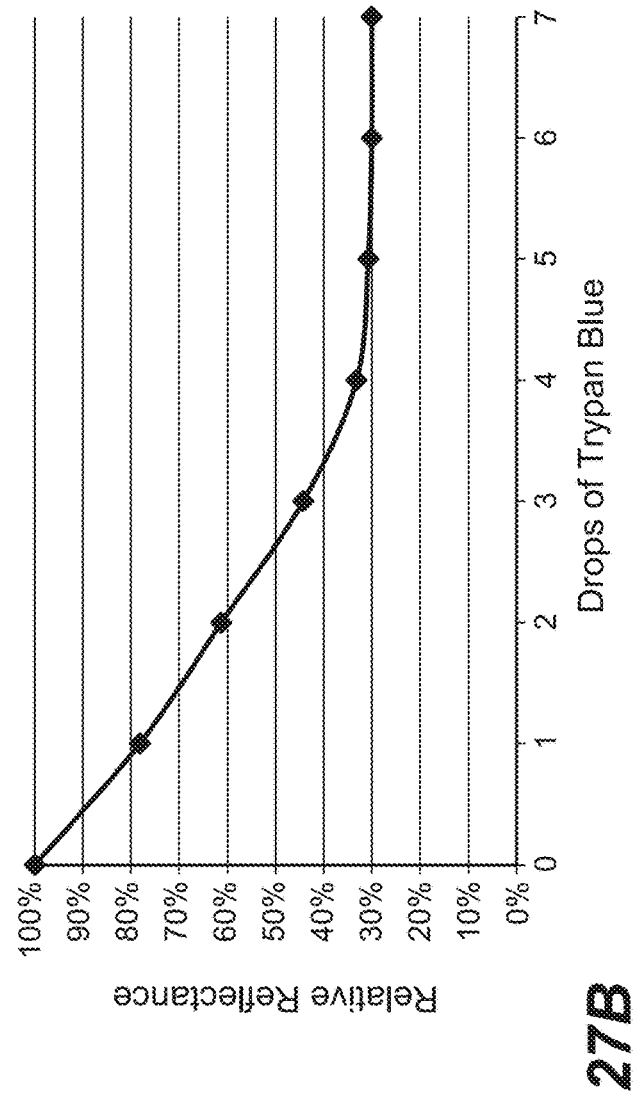
Figure 28A:
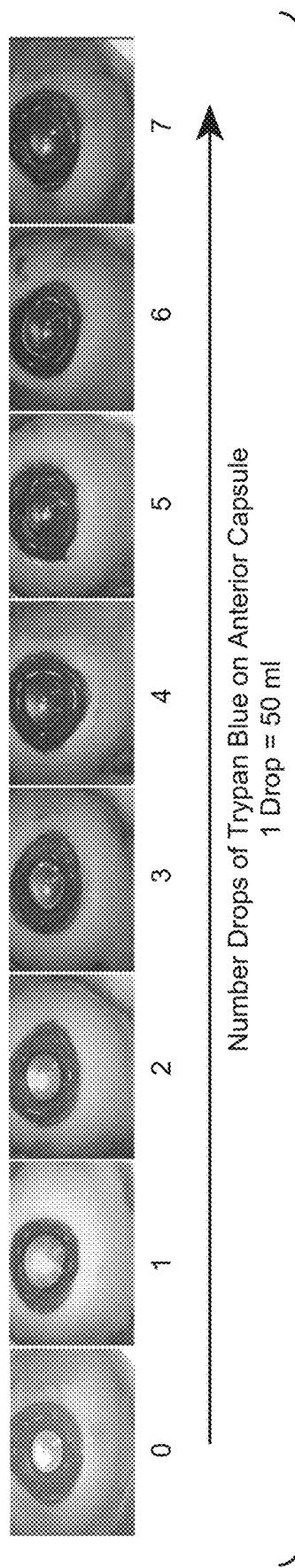
FIG. 28A and FIG. 28B show, respectively, example images and a plot of relative reflectance that illustrate a decreasing reflectance of narrow band (red) visualization laser illumination from a lens capsule as the amount of a light absorbing agent applied to the capsule is increased.
Figure 28B:
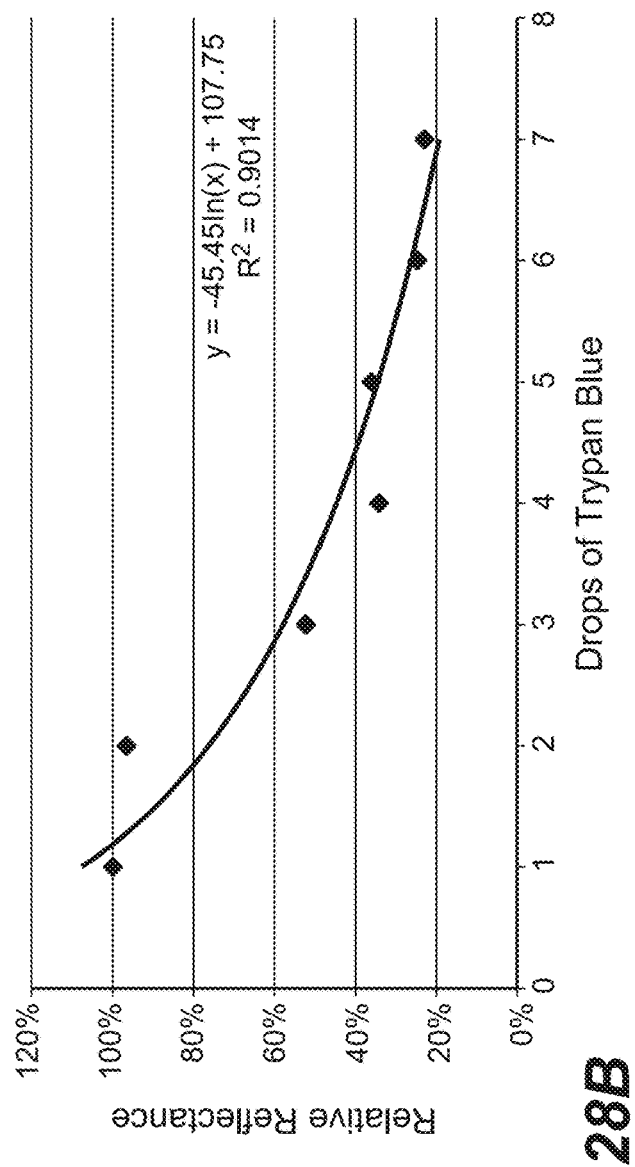

FIG. 27A shows example images and FIG. 27B shows a plot of relative reflectance that illustrate a decrease in the relative reflectance of broad band illumination from a lens capsule as the amount of light absorbing agent applied to the capsule is increased. Similarly, FIG. 28A shows example images and FIG. 28B shows a plot of relative reflectance that illustrate a decrease in the relative reflectance of narrow band (red) visualization laser illumination from a lens capsule as the amount of light absorbing agent applied to the capsule is increased.

In some variations, a computer implemented automatic anatomical recognition algorithm identifies the capsule region and optionally the iris and/or scleral regions of images of broad band light reflected from the eye before the light absorbing agent is applied to the capsule. Red, green, and/or blue reflection intensity values, optionally spatially averaged, are determined in the capsule region and optionally in the iris and/or the scleral regions of the images. Bright regions of the images in which the light detector (e.g., camera) may have saturated are processed independently and may or may not be used. The automatic recognition algorithm may adjust the illumination level to ensure accurate capsule identification and reflectance measurements, and optionally to reduce saturated regions. Similarly, the computer implemented automatic anatomical recognition algorithm identifies the capsule region and optionally the iris and/or scleral regions of images of broad band light reflected from the eye after the light absorbing agent is applied to the capsule. Red, green, and/or blue reflection intensity values, optionally spatially averaged, are determined in the capsule region and optionally in the iris and/or sclera regions of the images. Bright regions of the images in which the light detector (e.g., camera) may have saturated are processed independently and may or may not be used. The automatic recognition algorithm may adjust the illumination level to ensure accurate capsule identification and reflectance measurements, and optionally to reduce saturated regions.

Relative reflectance of red, green, and/or blue of the capsule relative to the iris may be calculated from the measured intensities for both the "before" and "after" images. Alternatively, or in addition, relative reflectance of red, green, and/or blue of the capsule relative to the scleral regions may be calculated from the measured intensities for both the "before" and "after" images. Alternatively, or in addition, relative reflectance of red, green, and/or blue of the capsule relative to the average total intensity for the image may be calculated from the measured intensities for both the "before" and "after" images. Alternatively, or in addition, relative reflectance of red, green, and or blue of the capsule for a fixed illumination intensity may be calculated from the measured intensities for both the "before" and "after" images. These variously determined reflectance values may be used to assess the quantity of light absorbing agent present in or on the capsule.

In other variations, a computer implemented automatic anatomical recognition algorithm identifies the capsule region and optionally the iris and/or scleral regions of images of narrow band (e.g., detection laser) light reflected from the eye before the light absorbing agent is applied to the capsule. Reflection intensity values, optionally spatially averaged, are determined in the capsule region and optionally in the iris and/or the scleral regions of the images. Bright regions of the images in which the light detector (e.g., camera) may have saturated are processed independently and may or may not be used. The automatic recognition algorithm may adjust the illumination level to ensure accurate capsule identification and reflectance measurements, and optionally to reduce saturated regions. Similarly, the computer implemented automatic anatomical recognition algorithm identifies the capsule region and optionally the iris and/or scleral regions of narrow band (e.g., detection laser) light reflected from the eye after the light absorbing agent is applied to the capsule. Reflection intensity values, optionally spatially averaged, are determined in the capsule region and optionally in the iris and/or scleral regions of the images. Bright regions of the images in which the light detector (e.g., camera) may have saturated are processed independently and may or may not be used. The automatic recognition algorithm may adjust the illumination level to ensure accurate capsule identification and reflectance measurements, and optionally to reduce saturated regions.

Relative reflectance of the capsule relative to the iris may be calculated from the measured intensities for both the "before" and "after" images. Alternatively, or in addition, relative reflectance of the capsule relative to the scleral regions may be calculated from the measured intensities for both the "before" and "after" images. Alternatively, or in addition, relative reflectance of the capsule relative to the average total intensity for the image may be calculated from the measured intensities for both the "before" and "after" images. Alternatively, or in addition, relative reflectance for a fixed illumination intensity may be calculated from the measured intensities for both the "before" and "after" images. These variously determined reflectance values may be used to assess the quantity of light absorbing agent present in or on the capsule.

In the reflectance measurement and analysis methods just described, automated anatomical recognition of a microscope view of the iris, capsule and sclera may be implemented by analyzing the image to determine three major regions. A primary region that is approximately circular represents the capsule or pupil, and typically has a diameter of about 4 mm to about 12 mm. A second region is an approximately circular band concentric to the primary region, and typically has a width of about 0.5 mm to about 5 mm. This second region represents the iris. The color texture from the image for this region may be from the reflection of the structured pigmented tissue, and may be utilized in the automated recognition. A third region is concentric to the primary and secondary regions, and represents the sclera. This region effectively reflects the illumination light and may have structured blood vessels that may be utilized in the automated recognition.

Figure 29:
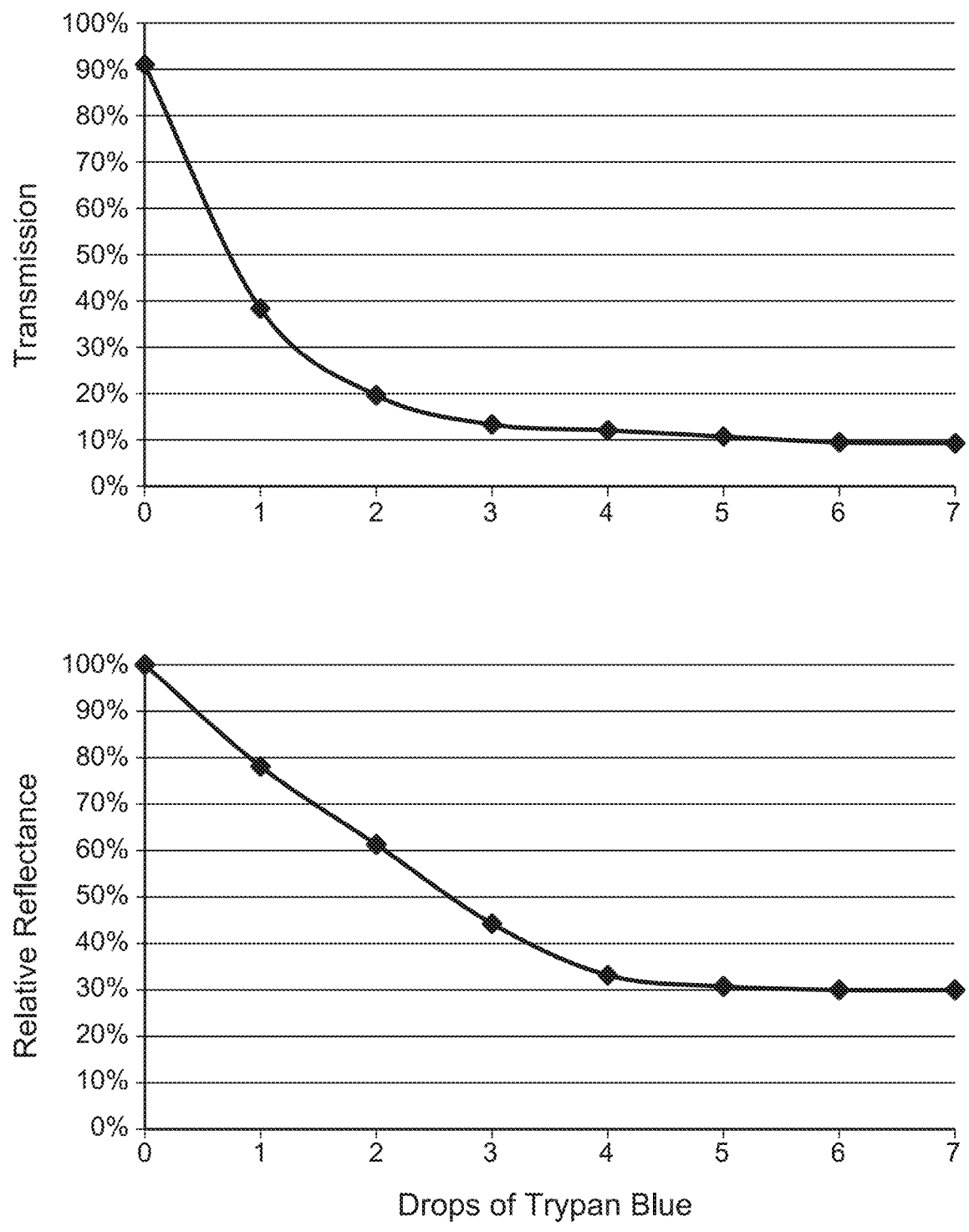
FIG. 29 shows plots of transmission at a treatment beam wavelength, and reflectance at another wavelength, through an anterior lens capsule treated with increasing amounts of a light absorbing agent.
Figure 30:
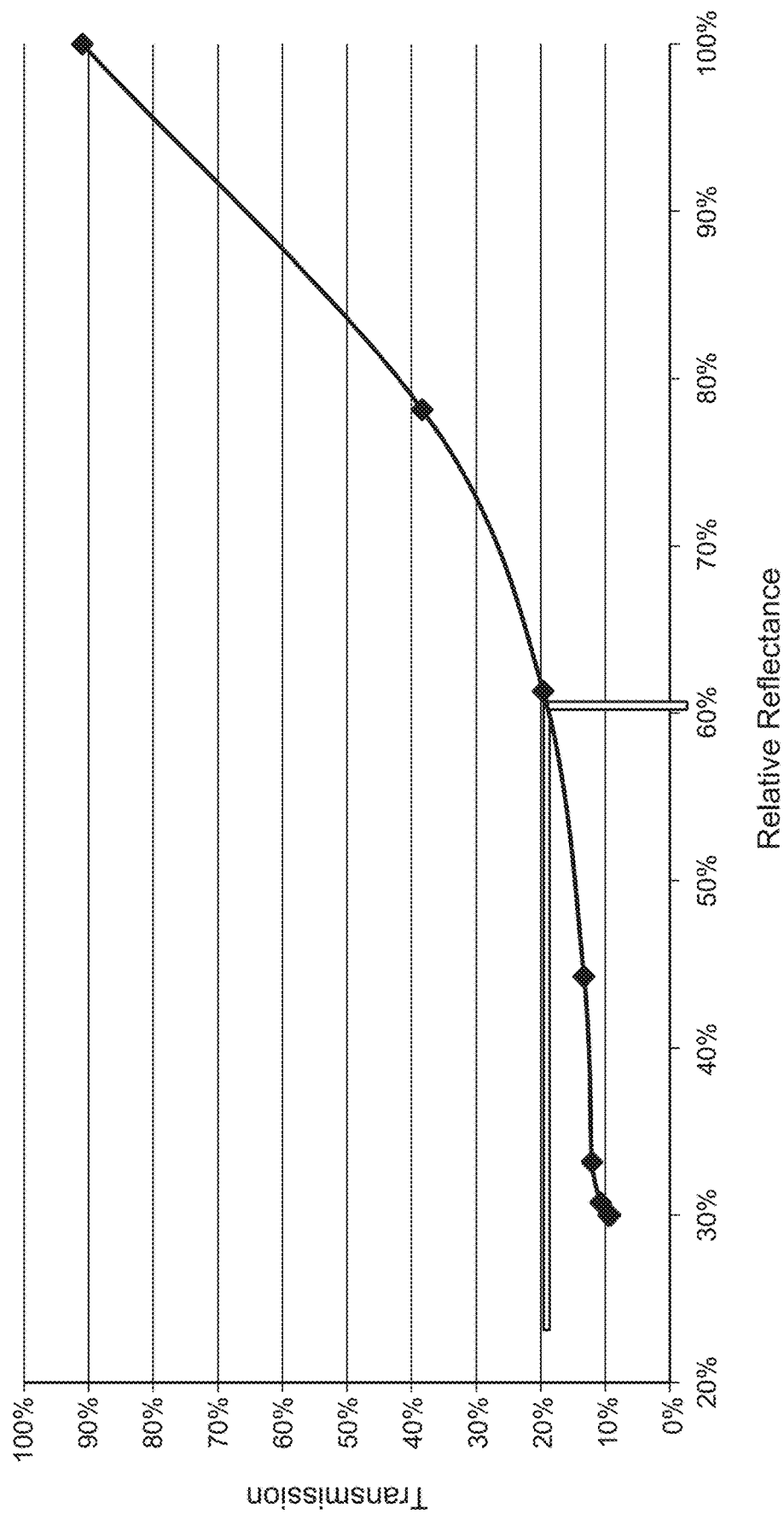
FIG. 30 shows a plot illustrating the correlation between the transmission and reflectance curves shown in FIG. 29.

If the light absorbing agent absorbs light at the wavelengths at which relative reflectance is measured, then the relative reflectance measurements will be positively correlated with transmission of the treatment beam through the capsule. That is, as the amount of light absorbing agent in the capsule is increased, both the relative reflectance (of a detection laser or of a component of broad band illumination, for example) and the transmission of the treatment beam will decrease. An example of this situation is shown in the plots of FIG. 29 and FIG. 30, for example.

Such a correlation between relative reflectance and treatment beam transmission may be measured on eyes from cadavers, for example, and then used to inform or control treatment on live patients.

For example, safe treatment may require that transmission of the treatment beam through the capsule be less than some predetermined threshold value, which correlates with a particular threshold relative reflectance value. In FIG. 30, for example, a 20% transmission threshold value corresponds to a 60% relative reflectance threshold value. If relative reflectance measured on the patient's eye after the light absorbing agent has been administered is less than the threshold reflectance value, then transmission of the treatment beam through the capsule is below the allowed limit and treatment may proceed. If relative reflectance is too high, then for example additional light absorbing agent may be administered until the relative reflectance is measured to be at or below the threshold relative reflectance value.

Alternatively or in addition, after the light absorbing agent has been administered, treatment parameters such as, for example, treatment laser power, wavelength, spot size, and/or scanning speed may be selected and/or controlled based on the relative reflectance measurements so that the treatment is optimally performed and the transmission of the treatment beam through the capsule remains below a predetermined threshold value throughout the treatment. The treatment device may for example utilize a look-up table mapping treatment parameters onto reflectance measurements.

The reflectance measurements may also be used, for example, to confirm that sufficient light absorbing agent is present along the treatment beam path to result in complete laser thermal separation of the anterior capsule, when the selected/preprogrammed treatment beam parameters are applied. This may be achieved for example by analyzing (as described above for example) images in the region that includes the complete treatment path, to ensure that the reflectance is below a predetermined (e.g., preprogrammed) value along the entire path.

In an alternative approach, the light absorbing agent may be detected by exciting and detecting fluorescence from the light absorbing agent. This may done, for example, using the treatment beam or an attenuated portion of the treatment beam. Such a measurement may optionally be made away from the treatment location to avoid depleting light absorbing agent required for the treatment scan. Fluorescence indicating the presence of the light absorbing agent may be observed or detected, for example, through a microscope integrated with the treatment device as described above.

This disclosure is illustrative and not limiting. Further modifications will be apparent to one skilled in the art in light of this disclosure and are intended to fall within the scope of the appended claims. For example, in some variations pulsed lasers may be used instead of continuous wave lasers to produce visualization and/or treatment laser beams in the methods and devices described above. Also, although the treatment beam is described above as causing thermal tissue separation along the closed curve without ablating anterior lens capsule tissue, devices and methods described herein may instead employ a treatment beam that causes separation of tissue along the closed curve by other laser-induced mechanisms such as laser-induced ablation of tissue, for example. In particular, the various treatment beam patterns, projected and virtual visualization patterns, methods for determining the visual axis of the eye, methods for assessing the orientation of a toric IOL, and related methods and devices described herein may be used with treatment lasers that cause separation of the anterior lens tissue along the closed path by any suitable mechanism.

What is claimed is:

1. A device for creating an opening centered on a visual axis of an eye in the anterior lens capsule of the eye, the device comprising:

a fixation laser outputting a visible light laser beam blinking at a frequency perceptible to a human patient, directed into the eye, and establishing the visual axis of the eye upon fixation by the patient on the visible light laser beam;

a treatment laser outputting a treatment laser beam;

a two-dimensional scanner on which the treatment laser beam is incident;

a first lens positioned before the two-dimensional scanner along the optical path of the treatment laser beam;

a second lens positioned after the two-dimensional scanner along the optical path of the treatment laser beam; and a scanner controller controlling the two-dimensional scanner, the scanner controller having a programmed scan profile for a predetermined treatment pattern in which the treatment laser beam is scanned to form a closed curve at the anterior lens capsule to form the opening;

wherein the first lens focuses the treatment laser beam to a first waist between the two dimensional scanner and the second lens, the second lens focuses the treatment laser beam to a second waist at the anterior lens capsule and the treatment laser beam expands from its second waist to be defocused on the retina of the eye, the second lens focuses the predetermined treatment pattern to a treatment pattern waist between the second lens and the eye, and the predetermined treatment pattern diverges in the eye and is consequently expanded in size and area on the retina compared to its size and area at the anterior lens capsule;

wherein the closed curve of the predetermined treatment pattern is centered on the blinking laser beam output by the fixation laser; and wherein the treatment laser beam has a wavelength absorbed by Trypan Blue or Indocyanine Green and a spot size of 100 microns to 350 microns.

2. The device of claim 1, wherein the treatment laser is a continuous wave laser, the treatment laser beam is scanned along the closed curve of the predetermined treatment pattern in a single pass, and the power of the treatment laser beam is constant along the closed curve.

3. The device of claim 1, wherein the treatment laser is a pulsed laser.

4. The device of claim 1, wherein the treatment laser beam has a diameter of 100 microns to 200 microns at the anterior lens capsule.

5. The device of claim 1, comprising a visualization laser outputting a visualization laser beam having a wavelength in the visible spectrum and incident on the two-dimensional scanner;

wherein the scanner controller has a programmed scan profile in which the visualization laser beam is scanned to form a predetermined visualization pattern at the anterior lens capsule to facilitate aligning the predetermined treatment pattern on the anterior lens capsule; and wherein at least a portion of the predetermined visualization pattern indicates desired boundaries of the opening to be created in the anterior lens capsule.

6. The device of claim 1, comprising a display programmed to present a predetermined virtual visualization pattern overlaid with a view of a surgical field of the anterior lens capsule to which the treatment laser beam is directed, to facilitate aligning the predetermined treatment pattern on the anterior lens capsule;

wherein at least a portion of the predetermined virtual visualization pattern indicates desired boundaries of the opening to be created in the anterior lens capsule.

7. The device of claim 1, comprising a detection laser outputting a detection laser beam having a wavelength that is reflected by Trypan Blue or Indocyanine Green.

8. The device of claim 1, comprising a detection laser outputting a detection laser beam having a wavelength that excites fluorescence from Trypan Blue or Indocyanine Green.

9. The device of claim 1, comprising a broad band light source outputting broad band illumination reflected by Trypan Blue or Indocyanine Green.

10. The device of claim 9, wherein the broad band illumination is white light.

* * * * *